US010231843B2

(12) United States Patent
Lee et al.

(10) Patent No.: US 10,231,843 B2
(45) Date of Patent: *Mar. 19, 2019

(54) SPINAL FUSION IMPLANTS AND DEVICES AND METHODS FOR DEPLOYING SUCH IMPLANTS

(71) Applicant: Benvenue Medical, Inc., Santa Clara, CA (US)

(72) Inventors: James Lee, San Mateo, CA (US); Jeffrey L. Emery, Emerald Hills, CA (US); Timothy McGrath, Fremont, CA (US); Laurent Schaller, Los Altos, CA (US); Andrew Huffmaster, Newark, CA (US); Ebrahim Mohammad Quddus, Fremont, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 15/276,147

(22) Filed: Sep. 26, 2016

(65) Prior Publication Data

US 2017/0027711 A1    Feb. 2, 2017

Related U.S. Application Data

(63) Continuation of application No. 13/803,322, filed on Mar. 14, 2013, now Pat. No. 9,480,574.

(51) Int. Cl.
*A61F 2/44*    (2006.01)
*A61F 2/46*    (2006.01)
(Continued)

(52) U.S. Cl.
CPC .......... *A61F 2/446* (2013.01); *A61B 17/8852* (2013.01); *A61F 2/442* (2013.01);
(Continued)

(58) Field of Classification Search
CPC ............... A61F 2/44; A61F 2002/4415; A61F 2002/448; A61F 2002/4485
(Continued)

(56) References Cited

U.S. PATENT DOCUMENTS

| 4,863,476 A | 9/1989 | Shepperd |
| 5,192,327 A | 3/1993 | Brantigan |

(Continued)

FOREIGN PATENT DOCUMENTS

| DE | 197 10 392 C1 | 7/1999 |
| EP | 1 157 676 A1 | 11/2001 |

(Continued)

OTHER PUBLICATIONS

International Search Report and Written Opinion for PCT Patent Application No. PCT/US2014/019246, dated Aug. 19, 2014.

(Continued)

*Primary Examiner* — Anu Ramana
(74) *Attorney, Agent, or Firm* — Cook Alex Ltd.

(57) ABSTRACT

Methods and apparatus are disclosed for distracting tissue. The devices and methods may include insertion of first and second elongated members into the space between two tissue layers, with an augmenting elongated member inserted therebetween to form a distraction device between the tissues to be distracted. The distraction device defines a generally annular configuration, with a locking member secured to one of the elongated members at a plurality of locations to maintain the distraction device in the generally annular configuration. The augmenting elongated member may be shorter than the first and second elongated members such that a window is defined between the proximal and distal ends of the augmenting elongated member when the distraction device and the first and second elongated members are in the generally annular configuration. Bone graft (Continued)

material or bone filler may be introduced into the interior of the distraction device through the window.

20 Claims, 14 Drawing Sheets

(51) Int. Cl.
*A61B 17/88* (2006.01)
*A61F 2/30* (2006.01)

(52) U.S. Cl.
CPC .......... *A61F 2/4455* (2013.01); *A61F 2/4601* (2013.01); *A61F 2/4611* (2013.01); *A61F 2002/3008* (2013.01); *A61F 2002/30018* (2013.01); *A61F 2002/3082* (2013.01); *A61F 2002/30092* (2013.01); *A61F 2002/30242* (2013.01); *A61F 2002/30383* (2013.01); *A61F 2002/30462* (2013.01); *A61F 2002/30507* (2013.01); *A61F 2002/30827* (2013.01); *A61F 2002/444* (2013.01); *A61F 2002/4415* (2013.01); *A61F 2002/4475* (2013.01); *A61F 2002/4623* (2013.01); *A61F 2220/0016* (2013.01)

(58) Field of Classification Search
USPC ............................................ 623/17.11–17.16
See application file for complete search history.

(56) References Cited

U.S. PATENT DOCUMENTS

| | | | |
|---|---|---|---|
| 5,306,310 | A | 4/1994 | Siebels |
| 5,374,267 | A | 12/1994 | Siegal |
| 5,397,364 | A | 3/1995 | Kozak et al. |
| 5,716,416 | A | 2/1998 | Lin |
| 5,755,797 | A | 5/1998 | Baumgartner |
| 6,039,761 | A | 3/2000 | Li et al. |
| 6,183,517 | B1 | 2/2001 | Suddaby |
| 6,436,142 | B1 | 8/2002 | Paes et al. |
| 6,454,806 | B1 | 9/2002 | Cohen et al. |
| 6,488,710 | B2 | 12/2002 | Besselink |
| 7,887,568 | B2 | 2/2011 | Ahlgren |
| 7,947,078 | B2 | 5/2011 | Siegal |
| 8,083,796 | B1 | 12/2011 | Raiszadeh et al. |
| 8,142,507 | B2 * | 3/2012 | McGuckin, Jr. ........ A61F 2/441 606/90 |
| 8,246,622 | B2 | 8/2012 | Siegal et al. |
| 2004/0064144 | A1 | 4/2004 | Johnson et al. |
| 2004/0230309 | A1 | 11/2004 | DiMauro et al. |
| 2004/0249464 | A1 | 12/2004 | Bindsell et al. |
| 2005/0021041 | A1 | 1/2005 | Michelson |
| 2005/0038517 | A1 | 2/2005 | Carrison et al. |
| 2005/0070911 | A1 | 3/2005 | Carrison et al. |
| 2005/0131541 | A1 | 6/2005 | Trieu |
| 2005/0273173 | A1 | 12/2005 | Gordon et al. |
| 2005/0278027 | A1 | 12/2005 | Hyde, Jr. |
| 2006/0030933 | A1 | 2/2006 | DeLegge et al. |
| 2006/0041258 | A1 | 2/2006 | Galea |
| 2006/0089646 | A1 | 4/2006 | Bonutti |
| 2006/0136064 | A1 | 6/2006 | Sherman |
| 2006/0189999 | A1 | 8/2006 | Zwirkoski |
| 2006/0287727 | A1 | 12/2006 | Segal |
| 2007/0173939 | A1 | 7/2007 | Kim et al. |
| 2008/0221687 | A1 | 9/2008 | Viker |
| 2008/0234687 | A1 | 9/2008 | Schaller et al. |
| 2009/0234454 | A1 | 9/2009 | Siegal |
| 2010/0198263 | A1 | 8/2010 | Siegal et al. |
| 2011/0125266 | A1 | 5/2011 | Rodgers et al. |
| 2011/0245926 | A1 | 10/2011 | Kitchen |
| 2011/0307063 | A1 | 12/2011 | Schaller et al. |
| 2012/0232664 | A1 | 9/2012 | Ulrich, Jr. et al. |
| 2013/0110239 | A1 | 5/2013 | Siegal et al. |

FOREIGN PATENT DOCUMENTS

| | | |
|---|---|---|
| FR | 2900814 A1 | 5/2006 |
| JP | 2002-28171 | 1/2002 |
| WO | WO 98/34552 A1 | 8/1998 |
| WO | WO 99/21500 | 5/1999 |
| WO | WO 00/74605 A1 | 12/2000 |
| WO | WO 2006/047587 A2 | 5/2006 |
| WO | WO 2006/072941 A2 | 7/2006 |
| WO | WO 2008/036505 A2 | 3/2008 |
| WO | WO 2008/084479 A2 | 7/2008 |
| WO | WO 2010/008353 A1 | 1/2010 |

OTHER PUBLICATIONS

Office Action dated Jul. 2, 2015 for U.S. Appl. No. 13/803,322.
Office Action dated Apr. 4, 2016 for U.S. Appl. No. 13/803,322.

* cited by examiner

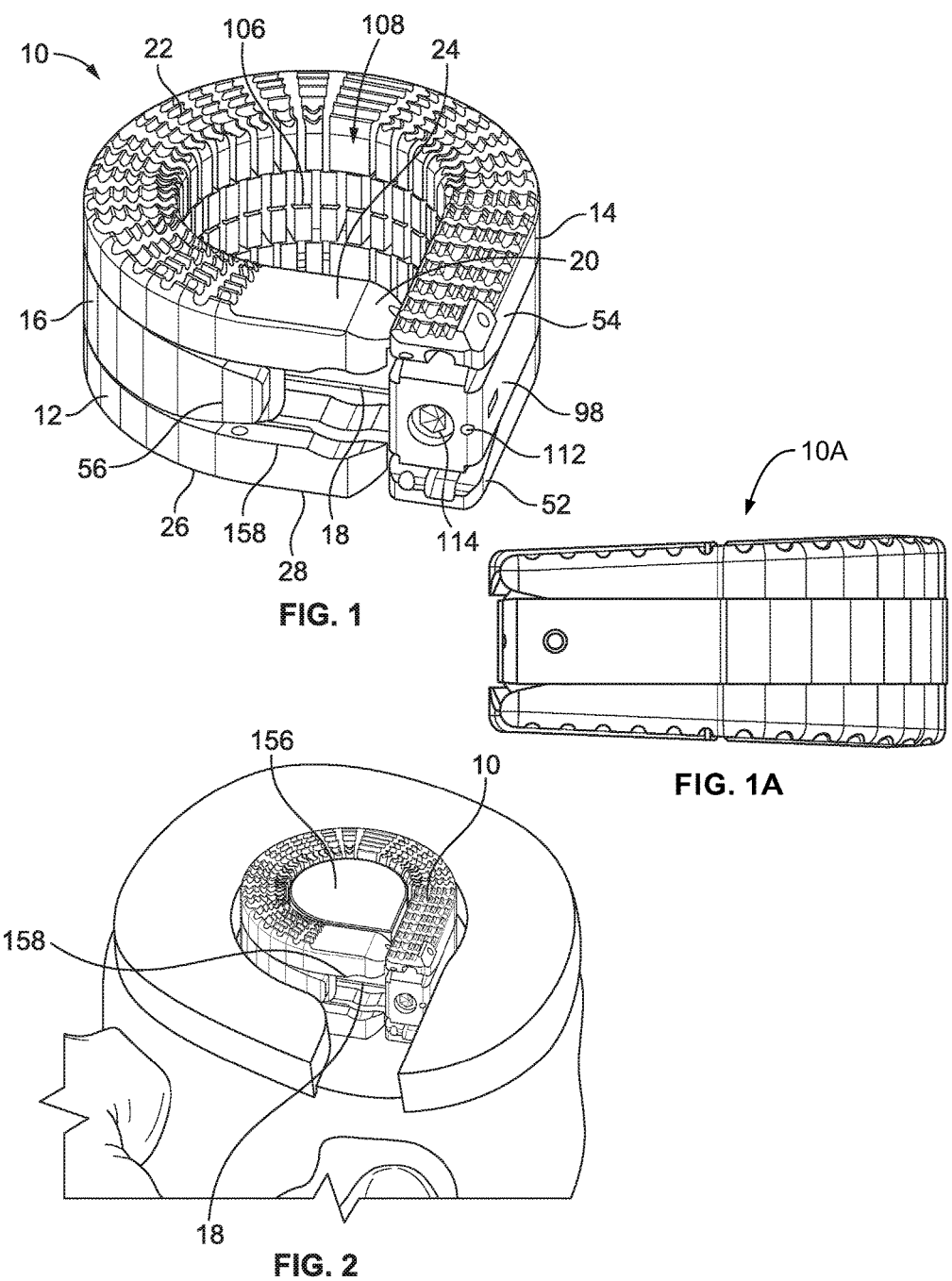

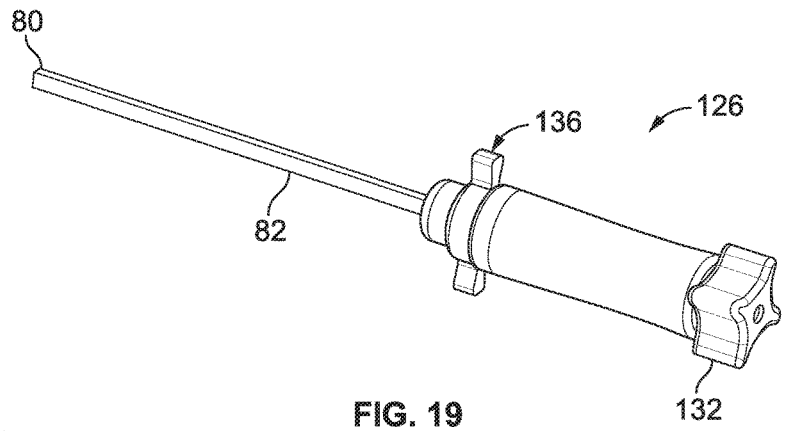
FIG. 19
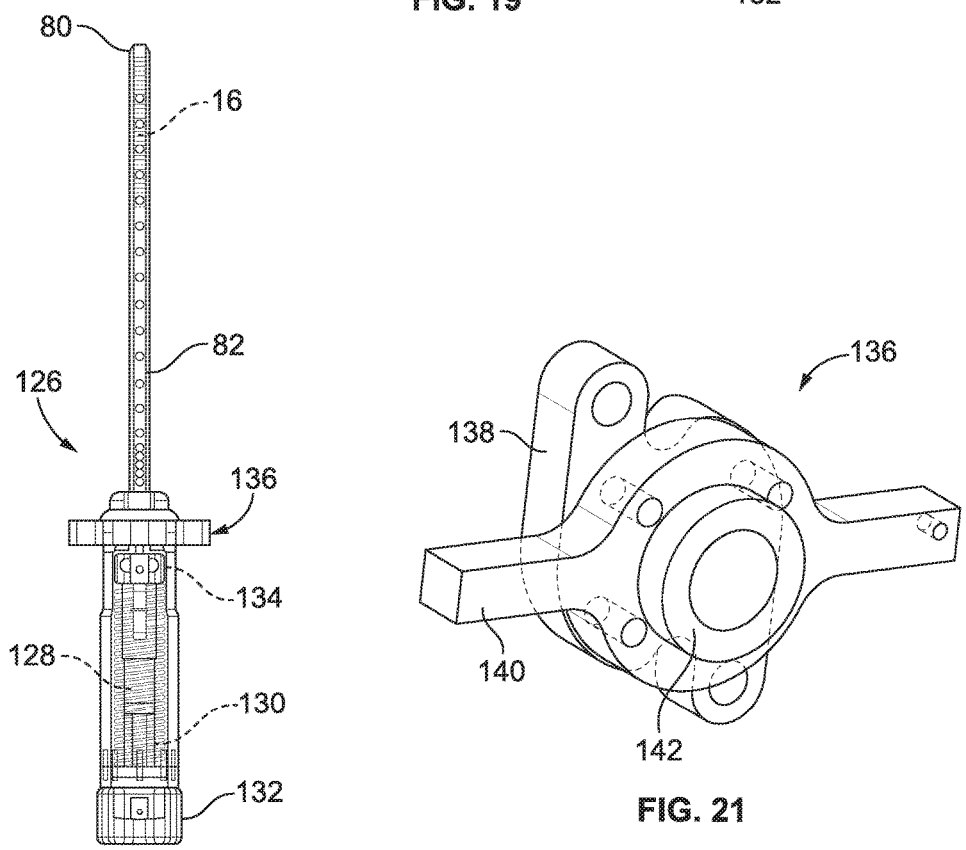
FIG. 20
FIG. 21

SPINAL FUSION IMPLANTS AND DEVICES AND METHODS FOR DEPLOYING SUCH IMPLANTS

The present application is a continuation of U.S. patent application Ser. No. 13/803,322, filed Mar. 14, 2013, now U.S. Pat. No. 9,480,574, the contents of which are incorporated herein by reference.

BACKGROUND

Field of the Disclosure

The present invention generally relates to apparatus and methods employed in minimally invasive surgical procedures and more particularly to various aspects of apparatus and methods for separating and/or supporting tissue layers, especially in the disc space of the spine.

Description of Related Art

A variety of physical conditions involve two tissue surfaces that, for diagnosis or treatment of the condition, need to be separated or distracted or maintained in a separated condition from one another and then supported in a spaced-apart relationship. Such separation or distraction may be to gain exposure to selected tissue structures, to apply a therapeutic pressure to selected tissues, to return or reposition tissue structures to a more normal or original anatomic position and form, to deliver a drug or growth factor, to alter, influence or deter further growth of select tissues or to carry out other diagnostic or therapeutic procedures. Depending on the condition being treated, the tissue surfaces may be opposed or contiguous and may be bone, skin, soft tissue, or a combination thereof.

One location of the body where tissue separation is useful as a corrective treatment is in the spinal column. Developmental irregularities, trauma, tumors, stress and degenerative wear can cause defects in the spinal column for which surgical intervention is necessary. Some of the more common defects of the spinal column include vertebral compression fractures, degeneration or disruption of an intervertebral disc and intervertebral disc herniation. These and other pathologies of the spine are often treated with implants that can restore vertebral column height, immobilize or fuse adjacent vertebral bones, or function to provide flexibility and restore natural movement of the spinal column. Accordingly, different defects in the spinal column require different types of treatment, and the location and anatomy of the spine that requires corrective surgical procedures determines whether an immobilizing implantable device or a flexible implantable device is used for such treatment.

In a typical spinal corrective procedure involving distraction of tissue layers, damaged spinal tissue is removed or relocated prior to distraction. After the damaged tissue has been removed or relocated, adjacent spinal tissue layers, such as adjacent bone structures, are then distracted to separate and restore the proper distance between the adjacent tissue layers. Once the tissue layers have been separated by the proper distance, an immobilizing or flexible device, depending on the desired treatment, is implanted between the tissue layers. In the past, the implantable treatment devices have been relatively large cage-like devices that require invasive surgical techniques which require relative large incisions into the human spine. Such invasive surgical techniques often disrupt and disturb tissue surrounding the surgical site to the detriment of the patient.

Therefore, there remains a need for implantable treatment devices and methods that utilize minimally invasive procedures.

Such methods and devices may be particularly needed in the area of intervertebral or disc treatment. The intervertebral disc is divided into two distinct regions: the nucleus pulposus and the annulus fibrosus. The nucleus lies at the center of the disc and is surrounded and contained by the annulus. The annulus contains collagen fibers that form concentric lamellae that surround the nucleus and insert into the endplates of the adjacent vertebral bodies to form a reinforced structure. Cartilaginous endplates are located at the interface between the disc and the adjacent vertebral bodies.

The intervertebral disc is the largest avascular structure in the body. The cells of the disc receive nutrients and expel waste by diffusion through the adjacent vascularized endplates. The hygroscopic nature of the proteoglycan matrix secreted by cells of the nucleus operates to generate high intra-nuclear pressure. As the water content in the disc increases, the intra-nuclear pressure increases and the nucleus swells to increase the height of the disc. This swelling places the fibers of the annulus in tension. A normal disc has a height of about 10-15 mm.

There are many causes of disruption or degeneration of the intervertebral disc that can be generally categorized as mechanical, genetic and biochemical. Mechanical damage includes herniation in which a portion of the nucleus pulposus projects through a fissure or tear in the annulus fibrosus. Genetic and biochemical causes can result in changes in the extracellular matrix pattern of the disc and a decrease in biosynthesis of extracellular matrix components by the cells of the disc. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disc hydraulic pressure, and ultimately to a loss of disc height. This loss of disc height can cause the annulus to buckle with non-tensile loading and the annular lamellae to delaminate, resulting in annular fissures. Herniation may then occur as rupture leads to protrusion of the nucleus.

Proper disc height is necessary to ensure proper functionality of the intervertebral disc and spinal column. The disc serves several functions, although its primary function is to facilitate mobility of the spine. In addition, the disc provides for load bearing, load transfer and shock absorption between vertebral levels. The weight of the person generates a compressive load on the discs, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disc height can have both local and global effects. Decreased disc height results in increased pressure in the nucleus, which can lead to a decrease in cell matrix synthesis and an increase in cell necrosis and apoptosis. In addition, increases in intra-discal pressure create an unfavorable environment for fluid transfer into the disc, which can cause a further decrease in disc height.

Decreased disc height also results in significant changes in the global mechanical stability of the spine. With decreasing height of the disc, the facet joints bear increasing loads and may undergo hypertrophy and degeneration, and may even act as a source of pain over time. Decreased stiffness of the spinal column and increased range of motion resulting from loss of disc height can lead to further instability of the spine, as well as back pain.

Radicular pain may result from a decrease in foraminal volume caused by decreased disc height. Specifically, as disc height decreases, the volume of the foraminal canal, through which the spinal nerve roots pass, decreases. This decrease may lead to spinal nerve impingement, with associated radiating pain and dysfunction.

Finally, adjacent segment loading increases as the disc height decreases at a given level. The discs that must bear additional loading are now susceptible to accelerated degeneration and compromise, which may eventually propagate along the destabilized spinal column.

In spite of all of these detriments that accompany decreases in disc height, where the change in disc height is gradual many of the ill effects may be "tolerable" to the spine and patient and may allow time for the spinal system to adapt to the gradual changes. However, the sudden decrease in disc volume caused by the surgical removal of the disc or disc nucleus may increase the local and global problems noted above.

Many disc defects are treated through a surgical procedure, such as a discectomy in which the nucleus pulposus material is removed. During a total discectomy, a substantial amount (and usually all) of the volume of the nucleus pulposus is removed and immediate loss of disc height and volume can result. Even with a partial discectomy, loss of disc height can ensue. Discectomy alone is the most common spinal surgical treatment, frequently used to treat radicular pain resulting from nerve impingement by disc bulge or disc fragments contacting the spinal neural structures.

The discectomy may be followed by an implant procedure in which a prosthesis is introduced into the cavity left in the disc space when the nucleus material is removed. Thus far, the most common prosthesis is a mechanical device or a "cage" that is sized to restore the proper disc height and is configured for fixation between adjacent vertebrae. These mechanical solutions take on a variety of forms, including solid kidney-shaped implants, hollow blocks filled with bone growth material, push-in implants and threaded cylindrical cages.

A challenge in the use of a posterior procedure to install spinal prosthesis devices is that a device large enough to contact the end plates and expand the space between the end plates of the same or adjacent vertebra must be inserted through a limited space. In the case of procedures to increasing intervertebral spacing, the difficulties are further increased by the presence of posterior osteophytes, which may cause "fish mouthing" or concavity of the posterior end plates and result in very limited access to the disc. A further challenge in degenerative disc spaces is the tendency of the disc space to assume a lenticular shape, which requires a relatively larger implant than often is easily introduced without causing trauma to the nerve roots. The size of rigid devices that may safely be introduced into the disc space is thereby limited.

While cages of the prior art have been generally successful in promoting fusion and approximating proper disc height, typically these cages have been inserted from the posterior approach, and are therefore limited in size by the interval between the nerve roots. Further, it is generally difficult to implant from the posterior approach a cage that accounts for the natural lordotic curve of the lumber spine.

It is desirable to reduce potential trauma to the nerve roots and yet still allow restoration or maintenance of disc space height in procedures involving vertebrae fusion devices and disc replacement, containment of the nucleus of the disc or prevention of herniation of the nucleus of the disc. In general minimally invasive surgical techniques reduce surgical trauma, blood loss and pain. However, despite the use of minimally invasive techniques, the implantation of cage devices for treating the spine typically involves nerve root retraction, an inherently high risk procedure. It is therefore desirable to reduce the degree of invasiveness of the surgical procedures required to implant the device, which may also serve to permit reduction in the pain, trauma, and blood loss as well as the avoidance and/or reduction of the nerve root retraction.

In minimally invasive procedures, to monitor placement, it is useful that implant devices inserted into spinal tissue be detectable using fluoroscopic imaging systems. However if a device is visible using X-ray technology, then the device can interfere with the detection and monitoring of spinal tissues, such as bone growing into the disc space after a vertebral fusion procedure. Additional advances would also be useful in this area.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a tissue distraction device includes first and second elongated members. The first and second elongated members are insertable between tissue layers and adapted to define a structure in situ having a dimensional aspect in a direction extending between the tissue layers. The tissue distraction device also includes an augmenting elongated member insertable between and in contact with the first and second elongated members to spread the first and second elongated members apart to increase the dimensional aspect of at least a portion of the structure in situ. The augmenting, first, and second elongated members are sufficiently flexible to change between a generally linear configuration and a generally less linear configuration. A locking member is configured to be secured to one of the elongated members at a plurality of locations to lock the augmenting, first, and second elongated members in the generally less linear configuration.

In another aspect, a tissue distraction device includes first and second elongated members defining a generally annular configuration. An augmenting member is fully received between the first and second elongated members and having a linear extent less than the linear extents of the first and second elongated members.

In yet another aspect, a method is provided for assembling a structure in vivo between two body tissue layers comprising first and second elongated members, an augmenting elongated member, and a locking member secured to one of the elongated members at a first location. The method includes delivering the first and second elongated members toward a location between two body tissue layers in a generally linear configuration to define at least a portion of a structure having a dimensional aspect in a direction extending generally from one of the body tissue layers to the other body tissue layer. The configurations of the first and second elongated members is changed to a generally less linear configuration. The augmenting elongated member is inserted between and in contact with the first and second elongated members to spread the first and second elongated members apart to increase the dimensional aspect of at least a portion of the structure. The locking member is secured to one of the elongated members at a second location to lock the first and second elongated members in the generally less linear configuration.

BRIEF DESCRIPTION OF THE DRAWINGS

FIG. 1 is a perspective view of a distraction device or support structure according to the present disclosure;

FIG. 1A is a side elevational view of a distraction device or support structure according to the present disclosure having a non-uniform thickness;

FIG. 2 is a perspective view of the distraction device of FIG. 1, deployed within a vertebral disc space;

FIG. 19 is perspective view of a delivery device suitable for delivering the distraction device of claim 1 to a work space;

FIG. 20 is a cross-sectional view of the delivery device of FIG. 19;

FIG. 21 is a perspective view of a shearing assembly of the delivery device of FIG. 19;

DESCRIPTION OF THE ILLUSTRATED EMBODIMENTS

Figure 3:
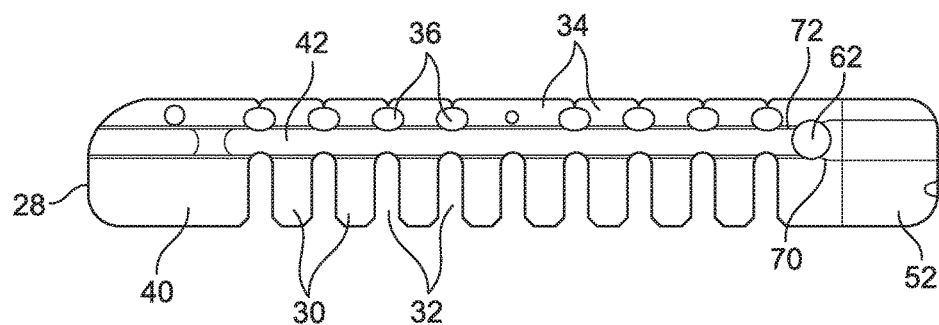
FIG. 3 is a top plan view of the lower elongated member of the distraction device of FIG. 1.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The devices and methods of the present invention provide multiple features of distraction devices, distraction device support structures and deployment systems that can be used to actively separate tissue layers by engaging them and forcing them apart, or to support the separation of tissue layers separated by the distraction device itself or by other devices or processes or a combination of these.

As used herein, the terms "distraction device" and "support structure" are intended to have a general meaning and is not limited to devices that only actively separate tissue layers, only support tissue layers or only both actively separate and support tissue layers. For example, the distraction device and support structure in general can be used to actively separate layers of tissue and then be removed after such separation, or the distraction device and the support structure could be used to support layers of tissue that have been previously separated by a different device. Alternatively, the distraction device and support structure can be used to actively separate the layers of tissue and remain in place to support the layers of tissue in order to maintain such separation. Unless more specifically set forth in the claims, as used herein, "distraction device" and "support structure" encompass any and all of these. In addition, it should be noted that the references to "first" and "second" members or devices are for convenience in the written description. They may be combined to provide a single distraction assembly or structure of selected distraction height, and the assembly is not limited to any particular number of "devices" or "members." In keeping with the broader aspects of the present invention the specific number of "devices" or "members" can be varied according to the intended usage or design considerations.

It should also be understood that various embodiments of the device, system and method of the present invention are illustrated for purposes of explanation in vertebral fusion procedures and/or replacement of removed discs. However, in its broader aspects, the various features of the present invention are not limited to these particular applications and may be used in connection with other tissue layers, such as soft tissue layers, although it has particular utility and benefit in treatment of vertebral conditions within intervertebral discs or disc spaces.

One embodiment of a distraction device or support structure or implant 10 is shown in FIGS. 1 and 2. The distraction device 10 shown in FIGS. 1 and 2 is comprised of a first or lower elongated member 12, a second or upper elongated member 14, an augmenting elongated member 16, and a locking member 18. The augmenting elongated member 16 cooperatively interacts with the first and second elongated members 12 and 14 to increase a dimensional aspect of the distraction device or support structure 10. The distraction device 10 is preferably comprised of elongated members made of biocompatible materials (including metals and polymers) that are suitable for long term implantation into human tissue where treatment is needed. The biocompatible materials may, for example, be calcium phosphate, tricalcium phosphate, hydroxyapatite, polyetheretherketone (PEEK), nylon, Nitinol (NiTi) or any other suitable biocompatible material. Suitable biocompatible material may also include PEEK with carbon fibers, polyethylenes of low, medium and or high densities, as well as nylons and blends of materials that contain nylons. It is also within the scope of the present disclosure for the elongated members to be at least partially comprised of one or more bioabsorbable materials, such as polyglycolic acid (PGA) or poly-L lactic acid (PLLA), for example. To the extent not contradicted by the present disclosure, elongated members according to the present disclosure may be manufactured, configured, and function generally according to the disclosure of U.S. Patent Application Publication No. 2008/0234687 to Schaller et al., which is incorporated herein by reference.

Elongated members according to the present disclosure may be manufactured using a number of techniques, including machining or milling techniques. Milling can include cutting elongated members from solid blocks or rods of PEEK or other suitable material. Elongated members may also be manufactured using molding techniques. Molding techniques include co-molding various materials together to form an elongated member, as well as molding a second material over a first material. Elongated members may also be manufactured by injection molding or extrusion processes. In addition, the elongated members of the present invention may be manufactured with electrical discharge machining processes and by rapid prototyping methods including fused deposition modeling (FDM) and stereo lithography (SLA) techniques.

Figure 4:
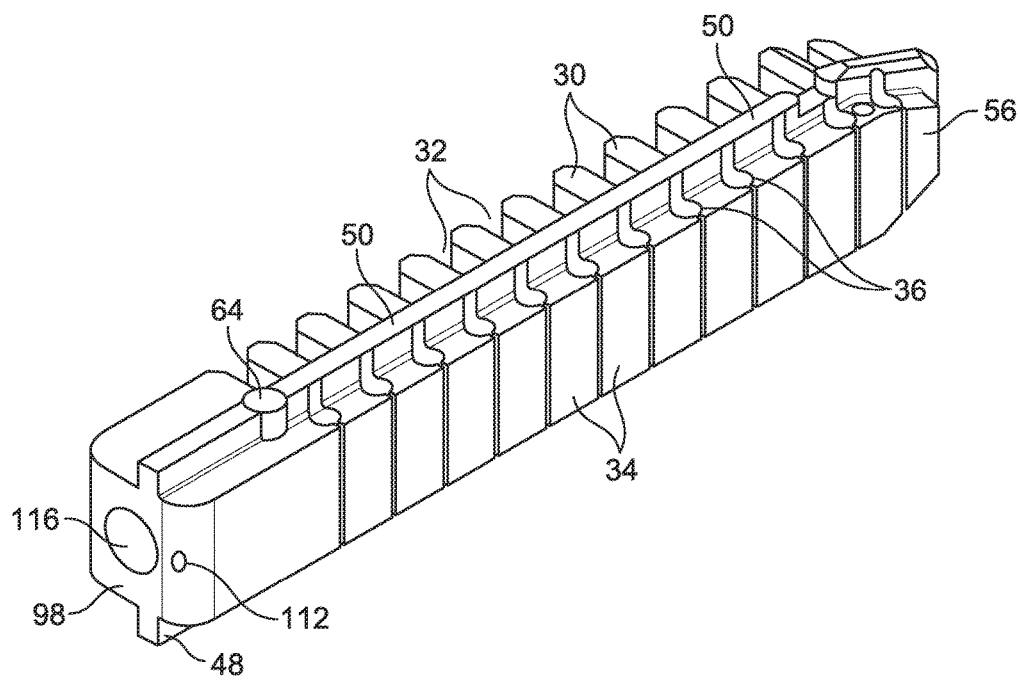
FIG. 4 is a perspective view of an augmenting member of the distraction device of FIG. 1.

Preferably, the elongated members which form the distraction device 10 have a generally linear configuration for insertion into tissue or between tissue layers. FIG. 3 shows the first or lower elongated member 12 in a generally linear configuration (with the understanding that the second or upper elongated member 14 may be substantially identical to or a mirror image of the first elongated member 12) and FIG. 4 shows the augmenting elongated member 16 in a generally linear configuration. The distal ends of the elongated members can have chamfer or incline or wedge features to ease the passage of the elongated member through tissue such as bone or vertebral disc material. For example, FIGS. 1 and 2 show a chamfer or incline feature 20 visible on the upper surface 22 of the distal end 24 of the second elongated element 14. It should be understood that the lower surface 26 of the distal end 28 of the first elongated element 12 may include a similar chamfer feature.

When deployed into or between tissue, the elongated members change configuration, preferably by flexing or bending, to a generally less linear configuration to define the distraction device or support structure 10. In a preferred embodiment, which is shown in FIGS. 1 and 2, the distraction device 10 is generally annular, with the first and second elongated members 12 and 14 also being generally annular and the augmenting elongated member 16 being generally arcuate, but non-annular, as will be described in greater detail herein. The elongated members of the distraction device 10 may include features that add flexibility to the elongated member to assist in bending or changing the configuration of the elongated member from a generally linear configuration to a less linear configuration and vice versa. For example, the elongated members may include lateral teeth 30 and intermediate slots or indents 32 (FIGS. 3 and 4) that aid in relieving stress and add flexibility to the elongated member. When the elongated member is deployed in spinal tissue, the slots 32 may also provide gaps for the introduction of bone graft materials, cements, or pharmaceutical compounds to the spinal tissues.

In some embodiments, the elongated members may also be designed with additional features that limit or control the nature of the bending or shape change that the elongated members may experience. For example, FIGS. 3 and 4 show a plurality of T-shaped members 34 on one lateral side of the elongated member (i.e., the lateral side opposite the aforementioned teeth 30 and slots 32, if provided), with the T-shaped members 34 having longitudinal extensions on their outer edge such that adjacent T-shaped members 34 almost touch each other, leaving a relatively narrow opening or aperture 36 at a more central location between adjacent T-shaped members 34. When the elongated member is bent toward the lateral side having the T-shaped members 34, the longitudinal extensions on adjacent T-shaped members 34 come into contact and provide resistance to further bending, thereby acting as a stop to limit further curvature. In contrast, the teeth 30 on the opposite lateral side of the elongated member lack such longitudinal projections and, therefore, the elongated member can be bent to a much greater degree in this direction before the teeth 30 come into contact with adjacent teeth 30 to limit further curvature. Also, it should be noted that by providing the T-shaped members 34 and intermediate opening or apertures 36, increased flexibility is provided that allows the elongated member to bend toward the opposite side (i.e., upwardly in the orientation of FIG. 3 or to the right in the orientation of FIG. 4).

Additional features may be added to enhance or limit the flexibility of the elongated members of the distraction devices, including grooves, slots, channels, and pockets and teeth or other extensions or members of various shapes. The slots, grooves, channels, and pockets may be placed, for example, in a linear pattern or spirally around the body of the elongated member. Through holes or apertures may also assist in providing flexibility as well as serve as lumens for various wires or filaments, as will be discussed in greater detail. The placement of a greater number of these features in one region of an elongated member can make that region more or less flexible than other regions of the device with fewer or different flexibility enhancing or limiting features. In this manner, selected regions of the elongated member will be easier or more difficult to bend or deflect to assist the shaping of the distraction device 10 in a desired configuration, such as a circular, rectangular, or oval shape. Alternatively, the flexibility features can be located uniformly along a segment or the whole of the elongated member to provide regions of uniform flexibility.

Flexibility of the elongated members may also be achieved or varied by fabricating the device from a combination of materials with different degrees of flexibility. For instance, by located more rigid material on one side of an elongated member, the elongated member may be easier to bend or deflect toward that side. Particularly, if the elongated member is preformed into a desired in situ configuration (e.g., a curved configuration) and temporarily straightened for insertion, the more rigid material may tend to retain the desired configuration to a greater degree than the other material and form the desired configuration when the elongated member is introduced into the work space. Also, the elongated member can have alternating or different sections along its length that are made of different materials having different rigidity.

In another aspect of the present disclosure, the elongated members preferably have the ability to recover from temporary deformation. As noted previously, the elongated member(s) may be pre-set or pre-formed into a desired in situ shape and then temporarily reshaped, such as by straightening, for insertion. In this aspect, for instance, a pre-shaped elongated member may tend to recover its shape more quickly or completely in body-temperature spinal tissue after being in a less-curved condition during shipping and storage inside of a deployment cannula. In other embodiments, due to plastic creep or other material characteristics, the elongated members may not recover their original shape after extended deformation in the cannula, and an external force may be used to shape the elongated member after it is at least partially inserted into the work space.

In a specific example, elongated members manufactured from polymeric materials such as PEEK may be pre-shaped by placing the elongated member in a metal fixture or jig having a desired shape, such as an annular or arcuate shape, and then heating the elongated member to relieve the bending stress. For instance, the elongated member can be treated for about 5 minutes at about 160° C. For many polymeric materials, such as PEEK, the pre-shaping process biases the elongated member toward a desired shape yet still allows the elongated member to be deformed either in the cannula or in situ after the elongated member is inserted into a work space. In some embodiments, such as where the elongated members are comprised at least in part of PEEK, the elongated members do not have shape memory material properties. Consequently, in some embodiments, particularly when PEEK is used, the elongated member does not return to its original shape without the additional application of an external force to shape the member. Such external force may be applied, for example, by a pull wire, as will be described in more detail.

In some embodiments, the deformation of the elongated members is constrained in a first axis and allowed in a plane at an angle to the first axis to allow deflection in a different plane. For instance, in FIG. 2, a generally annular distraction device 10 is shown in a vertebral disc. As used herein, the term "annular" is not limited to substantially circular distraction devices and elongated members, but may include other closed shapes, such as ovals and rectangles, or substantially closed versions of such shapes. The distraction device 10 is formed by the aforementioned three elongated members 12, 14, and 16 and is relatively rigid in the direction (e.g., a vertical direction when standing) extending between two tissues layers, i.e. the adjacent vertebra. The distraction device 10 is resistant to deflection in a direction parallel to the longitudinal axis of the spine due to the relatively solid, continuous structure of the elongated members along this axis. Consequently, due to the structure of the elongated members forming the distraction device 10 of FIG. 2, no deflection or only limited deflection is allowed in the direction of distraction. In certain embodiments, the distraction device or implant 10 does not substantially compress under vertical forces that the human spine normally endures, such as, but not limited to, up to about 1000 N. In contrast, the elongated members are relatively more flexible in the plane perpendicular to the direction of distraction to allow the elongated members to be shaped as desired, such as curved or deflected to conform to the shape of the space into which they are implanted.

Looking more particularly at the augmenting elongated member 16, it is configured to be inserted and slid between the first and second elongated members 12 and 14 to increase the height of or otherwise augment the distraction device 10. The degree of height increase of the distraction device 10 is dependent upon the height of the augmenting elongated member 16. For instance, a thicker augmenting elongated member (i.e., an augmenting elongated member having a relatively great height) will cause a greater increase in the height of the distraction device than a thinner augmenting elongated member (i.e., an augmenting elongated member having a relatively small height). In embodiments inserted into the disc space to distract adjacent vertebral bodies, the height of the distraction device 10 (which is generally equal to the combined heights of the bodies of the constituent elongated members) is preferably sufficient to restore the disc to its normal height or thereabout, which will depend on the size of the patient and the disc's location in the spinal column. The height of the distraction device 10 can be, for example, from about 5 mm to about 15 mm. More particularly, the height can be from about 7.5 mm to about 13.5 mm, or about 9 mm to about 12 mm and ranges therein. For relatively short individuals or children, the disc size and, consequently, the height of the support structure can be, for example, from about 5 mm to about 7 mm. For relatively tall individuals, the disc height and, consequently, the height of the support structure can be, for example, from about 9 mm to about 15 mm or greater potentially. In other applications, the dimensions (including the heights) of the individual elongated members and the resulting distraction device may vary without departing from the scope of the present disclosure.

In one embodiment, the thickness of the augmenting elongated member can be different along its length to cause different amounts of additional distraction along the length of the distraction device. For instance, the proximal portion of the augmenting member may be thicker (taller) than the distal portion of the augmenting member, in which case the increase in the height of the proximal portion of the distraction device will be greater than the augmentation in the height of the distal portion of the device. The ability to create a greater increase in height in one region of a distraction device allows for adjustments in the curvature of the spine of a patient. For instance, a collapsed disc in the lumbar region of the spine can result in the loss of the normal lordosis in the lumbar region of the spine. The insertion of an augmenting elongated member of variable thickness/height between upper and lower elongated members deployed in a collapsed lumbar disc can restore the lumbar disc to the more normal morphology of a greater height on its anterior region as compared to its posterior region. In such a situation, the augmenting member may have a greater height at its central region between the distal and proximal ends than at either the proximal end or distal end. FIG. 1A illustrates an exemplary distraction device 10A having a non-uniform thickness.

Preferably, once augmented, the height of the distraction device 10 is fixed and is not adjustable or variable, while the augmenting member 16 is preferably fixed in position between the first and second elongated members 12 and 14 and not removable. The first and second elongated members 12 and 14 may have corresponding contoured surfaces or features that mechanically or frictionally cooperate or mate to assist in maintaining the positions of the first and second elongated members 12 and 14 relative to each other and within a work space to increase the stability of the distraction device 10. For example, in one embodiment, the upper surface 22 of the second elongated element 14 (as shown in greater detail in FIGS. 5-7) and the lower surface 26 of the first elongated element 12 include protrusions or ribs or teeth 38 or is otherwise textured, which may be advantageous when the first and second elongated members 12 and 14 are in their generally less linear configuration to define the distraction device 10. In particular, such textured surfaces may be advantageous in that contact between the protrusions 38 and the tissue to be distracted and/or supported may help to anchor the elongated member (and, hence, the distraction device 10) in position. For example, when the distraction device 10 contacts a vertebral body, the protrusions 38 may dig into the vertebral body for improved traction, thereby decreasing the risk of movement of the distraction device 10 after implantation.

Figure 8:
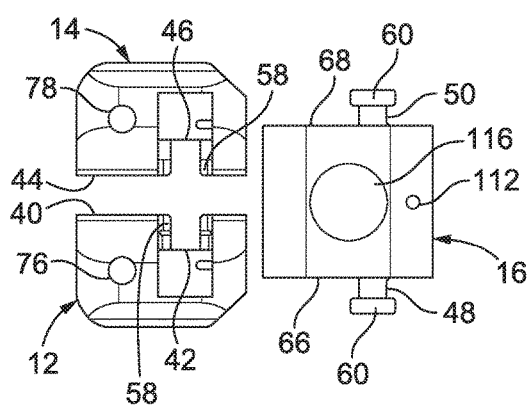
FIG. 8 is an end view of the two elongated members and the augmenting member of the distraction device of FIG. 1, in a disassembled condition.
Figure 9:
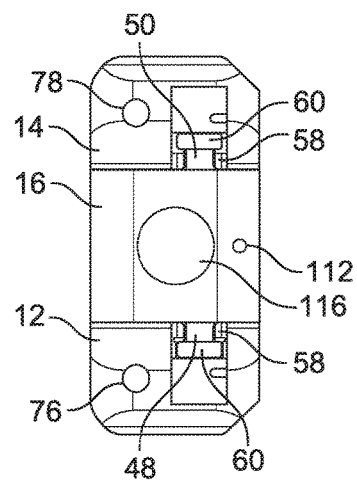
FIG. 9 is an end view of the two elongated members and augmenting member of FIG. 8, in an assembled condition.

The top side or surface 40 of the first elongated member 12 may contain a contoured portion 42 (FIGS. 3, 8, and 9), while the bottom side or surface 44 of the second elongated member 14 may also include a contoured portion 46, as shown in FIGS. 8 and 9. The augmenting elongated member 16 also may include a bottom contoured portion or surface 48 and a top contoured portion or surface 50, as shown in FIGS. 4, 8, and 9. In the illustrated embodiment, the contoured portions 48 and 50 of the augmenting elongated member 16 are protrusions or raised ribs that are configured to mate with the contoured portions 42 and 46, respectively, of the first and second elongated members 12 and 14. In the illustrated embodiment, the contoured portions 42 and 46 of the first and second elongated members 12 and 14 are indentations or slots or grooves in the top surface 40 of the first elongated member 12 and the bottom surface 44 of the second elongated member 14. Alternatively, the bottom and top surfaces of the augmenting elongated member may include indentations or slots or grooves that are configured to mate with a protrusion or rib on the top surface of the first elongated member and the bottom surface of the second elongated member, respectively.

Figures 10, 11:
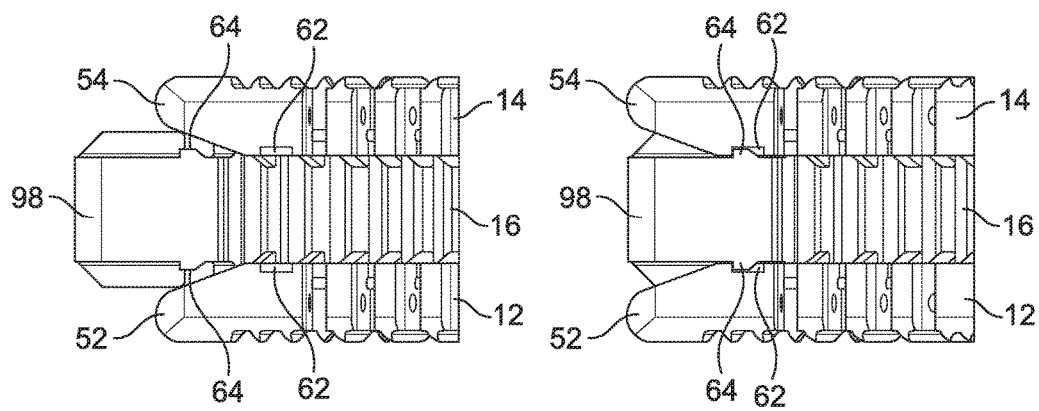
FIG. 10 is a side view of proximal ends of the two elongated members and augmenting member of FIG. 8, in a partially assembled condition.
FIG. 11 is a side view of proximal ends of the two elongated members and augmenting member of FIG. 8, in an assembled condition.

As shown in FIGS. 8 and 9, the cooperation between the raised ribs and grooves in the facing surfaces between of the elongated members also can function as a guide or guide track that directs the augmenting elongated member 16 between the first and second elongated members 12 and 14. As seen in FIGS. 10 and 11, the proximal ends 52 and 54 of the first and second elongated members 12 and 14 can also be ramped or widened to provide a larger opening, thereby easing the entry of the augmenting elongated member 16 (which may have a tapered or wedge-shaped distal end 56, as noted above) between the first and second elongated members 12 and 14. Furthermore, any of the elongated members may have additional mating or guiding surfaces which provide added stability to the resulting distraction device or implant support structure 10.

In a preferred embodiment, the raised ribs 48 and 50 and grooves 42 and 46 are configured to prevent vertical separation of the elongated members. For example, the illustrated raised ribs 48 and 50 are generally T-shaped, while the grooves 42 and 46 have relatively narrow necked-down portions 58. As the augmenting elongated member 16 is inserted between the first and second elongated members 12 and 14, the relatively wide heads 60 of the raised ribs 48 and 50 are received by the grooves 42 and 46, with the necked-down portions 58 positioned between the wide heads 60 and the body of the augmenting elongated member 16. By such a configuration, the rib heads 60 and the necked-down portions 58 of the grooves 42 and 46 prevent the elongated members from being vertically separated after at least partial insertion of the augmenting elongated member 16 between the first and second elongated members 12 and 14. This locking mechanism may assist in preventing the elongated members from slipping relative to one another in response to the stresses a patient's normal movements place on the implant 10.

FIGS. 10 and 11 also show another optional locking feature for securing the elongated members together. In the illustrated embodiment, the first and second elongated members 12 and 14 include recesses 62 into which locking protrusions 64 of the augmenting member 16 can enter to lock the augmenting member 16 into a desired longitudinal orientation relative to the first and second elongated members 12 and 14. When fully engaged, all three elongated members are substantially locked against relative movement. Preferably, the locking protrusions 64 enter into the recesses 62 to lock the elongated members together when the augmenting elongated member 16 has been fully inserted between the other two elongated members 12 and 14, but it is also within the scope of the present disclosure for the elongated members to lock together prior to the augmenting elongated member 16 being fully received between the other two elongated members 12 and 14. For example, the elongated members may be configured such that the augmenting elongated member 16 is not advanced fully into the space between the other two elongated members 12 and 14, but is instead locked in place with a portion (e.g., a proximal end) remaining outside of the space between the other two elongated members 12 and 14.

The guiding of the locking protrusions 64 into the recesses 62 may be assisted by locating them along the contoured surfaces of the associated elongated member. As seen in FIGS. 3 and 4, for example, the recess 62 and groove 42 in the upper surface 40 of the first elongated member 12 are aligned, thereby allowing the groove 42 to act as a guide in which the locking protrusion 48 on the bottom surface 66 of the augmenting elongated member 16 slides distally to seat within the recess 62, as shown in FIG. 11. FIG. 4 shows how the protrusion 64 and raised rib 50 of the upper surface 68 of the augmenting elongated member 16 are similarly aligned, as may be the protrusion 64 and raised rib 48 of the lower surface 66 of the augmenting elongated member 16.

As illustrated, the locking protrusions 64 may be cylindrically shaped, but it may be otherwise shaped without departing from the scope of the present disclosure. If provided as a cylinder, the diameter of the locking protrusion 64 may be greater than the width of the associated raised rib 48, 50 (FIG. 4) and of the associated groove 42, 46 at the point 70 it meets the recess 62 into which the protrusion 64 is to be seated (FIG. 3). By such a configuration, the protrusion 64 may be pressed into the recess 62, but will resist being retracted therefrom due to the relatively narrow entry point 70. The portion 72 of the groove 42, 46 immediately distal the recess 62 may also be relatively narrow, thereby preventing over-advancement of the protrusion 64 beyond the recess 62.

The locking protrusions 64 may be any suitable size or material, such as cylinders or pins made of a radiopaque material (e.g., tantalum or gold or platinum) with a diameter ranging from about 0.25 mm to about 2 mm. By providing the locking protrusions 64 as radiopaque members, they assist the surgeon in positioning the elongated members in situ. For a similar effect, the interlocking recesses 62 may be lined with tantalum or another radiopaque material. In other embodiments, other portions of the elongated members may be radiopaque to further assist in determining the locations of the elongated members in situ. In one exemplary embodiment, the elongated members are manufactured from radiolucent materials, such as PEEK (which may be a preferred material), polyetherketoneketone (PEKK), nylon and ultra-high molecular weight polyethylenes (UMPE). By providing discrete radiopaque regions or markers in known locations within the elongated members, the surgeon may determine the locations and relative orientations of the elongated members in situ.

Figure 12:
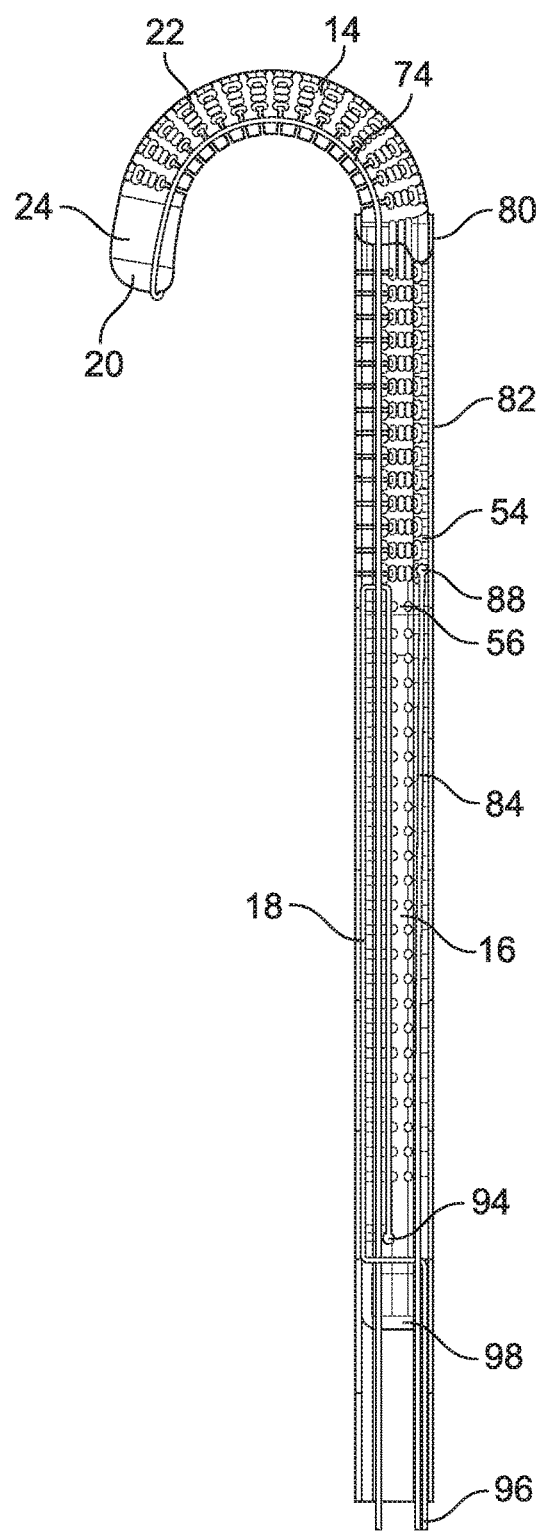
FIG. 12 is a top plan view of the elongated members of the distraction device of FIG. 1 at least partially positioned within a deployment cannula.
Figure 13:
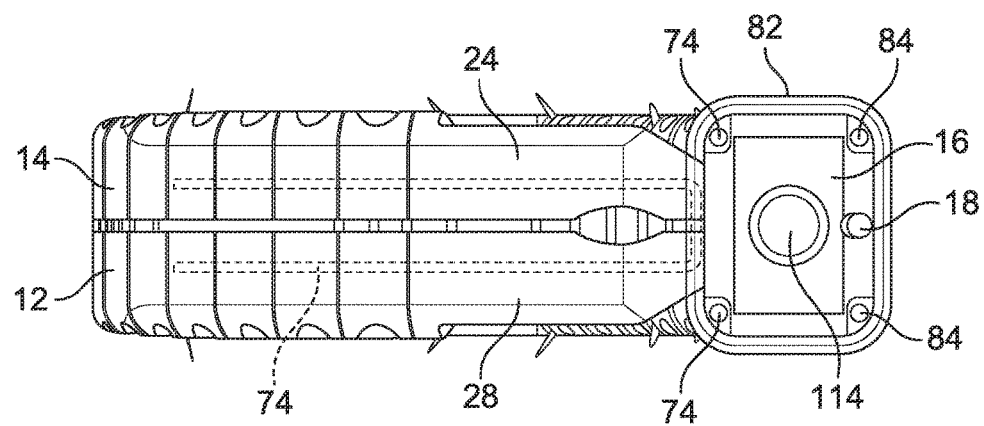
FIG. 13 is an end view of the elongated members and cannula of FIG. 12.
Figure 14:
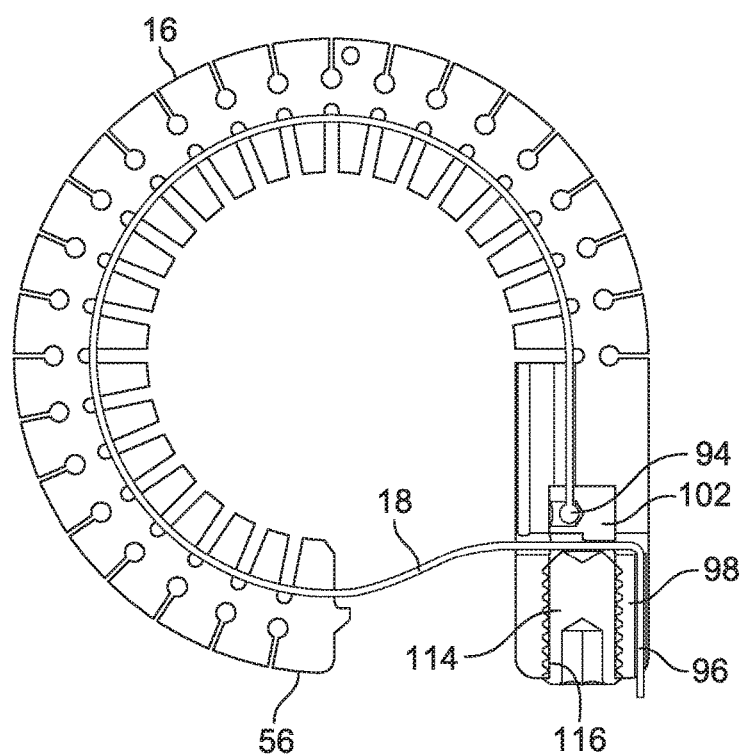
FIG. 14 is a cross-sectional top plan view of the augmenting elongated member of the distraction device of FIG. 1.

In addition to the foregoing features, the elongated members may further include internal cavities or passages or lumen for receiving various wires or filaments. For example, as described above, the shape of the distraction device 10 may be assisted, controlled, and/or adjusted as the elongated members are being deployed between the tissues to be distracted. The forces required to control the shape of the elongated members are preferably compatible with typical hand-held delivery systems and tools. For instance, the shape of an elongated member may be controlled with pull wire systems deployed either inside the elongated member and/or outside the elongated member. In the illustrated embodiment, the shape of the first and second elongated members 12 and 14 is controlled during insertion by applying a greater force to one side of the elongated members than is applied to the other side using a pull wire 74 (FIGS. 12 and 13). The application of unequal force causes the elongated members 12 and 14 to curve in a particular direction (i.e., to the left in the orientation of FIG. 12).

In the embodiment of FIGS. 12 and 13, the pull wire 74 passes through both the first and second elongated members 12 and 14. The pull wire 74 may pass through a wire lumen 76, 78 of each of the first and second elongated members 12 and 14 like those shown in FIGS. 8 and 9 or, alternatively, through a wire channel or slot that is not fully enclosed. As shown in FIG. 13, the pull wire 74 passes out of the distal end of one wire lumen, and then loops back into the other wire lumen. The pull wire 74 may be a single wire or filament or a braid or weave comprising multiple wires or filaments and may be made of any flexible material that can be used to exert a force along the length of the first and second elongated members 12 and 14, such as steel, Nitinol, fiber (both synthetic and natural), or the like. In the illustrated example shown in FIGS. 8, 9, 12, and 13, the pull wire 74 is on the left side of the first and second elongated members 12 and 14 (when considered from the proximal ends of the elongated members) such that a proximally directed force (e.g., pulling one or both of the ends of the wire 74, will cause the first and second elongated members 12 and 14 to curve to the left. Alternatively, systems in which a push or a distally directed force, applied through a rigid pusher or the like could be provided to the first and second elongated members 12 and 14 to cause them to curve in a desired direction.

In systems such as the one illustrated in FIGS. 12 and 13, which include a pull wire 74 that passes through both the first and second elongated members 12 and 14, the pull wire 74 also tends to prevent the first and second members 12 and 14 from separating during deployment into the work space. In particular, a pull wire 74 extending through both the first and second elongated members 12 and 14 may also allow pull force to be exerted to maintain the position of the first and second elongated members 12 and 14 adjacent to the distal end 80 of a deployment cannula 82 while the augmenting member 16, is being inserted between the first and second elongated members 12 and 14. In particular, the insertion of the augmenting elongated member 16 between the first and second elongated members 12 and 14 can create a repulsive force that tends to push the first and second elongated members 12 and 14 away from both the cannula 82 and the augmenting member 16. The force exerted by the pull wire 74 and the force of friction between the surfaces of the first and second elongated members 12 and 14 and the surrounding tissues, such as the endplates of the vertebrae above and below a disc, can also serve to resist this repulsive force.

Figure 5:
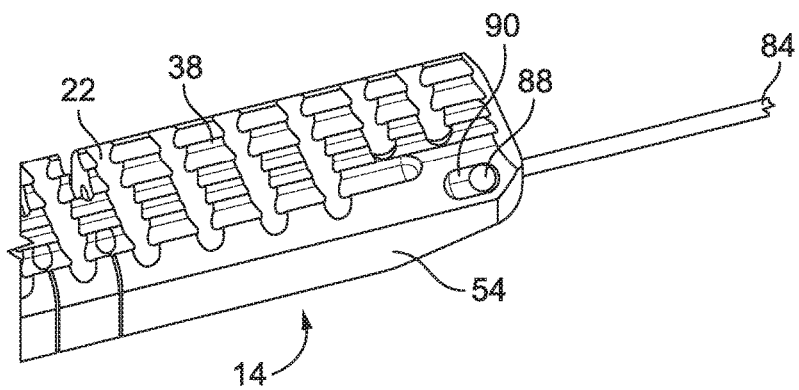
FIGS. 5-7 are perspective views of a proximal end portion of the upper elongated member of the distraction device of FIG. 1, with an associated anchor member being shown in different positions.
Figure 6:
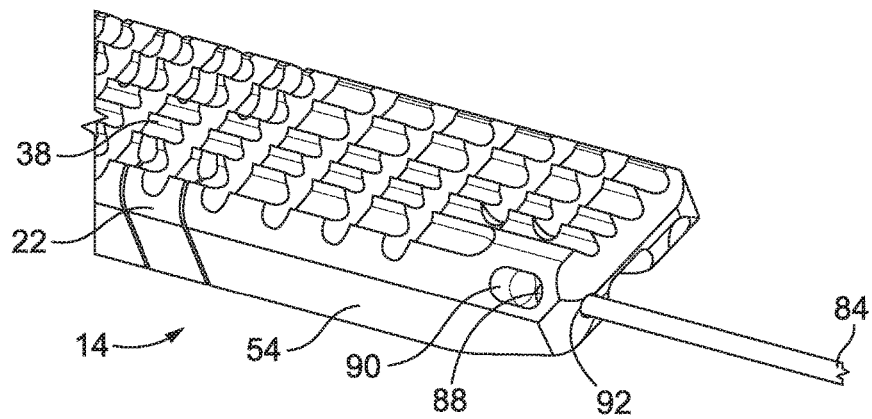
Figure 7:
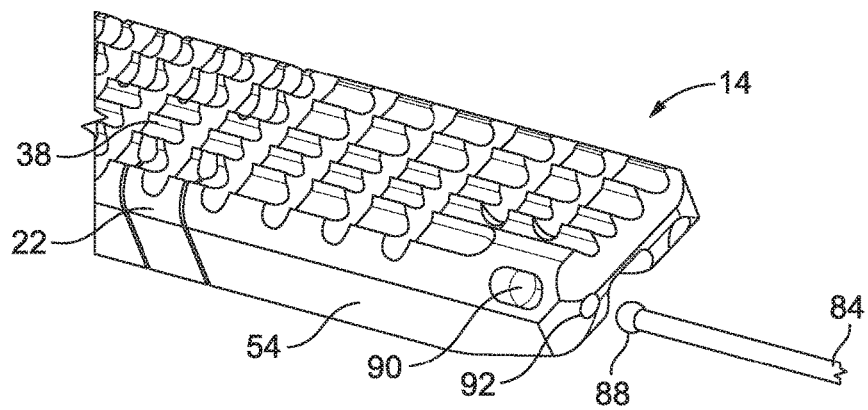

In other embodiments, including the illustrated embodiment, a separate mechanism may be provided to maintain the position of the first and second elongated members 12 and 14 with respect to the deployment cannula 82 while the augmenting elongated member 16 is inserted therebetween. As shown in FIGS. 5-7 and 12, an anchoring or tethering system or wires 84 can be used to hold the first and second elongated members 12 and 14 aligned with the distal end 80 of the delivery cannula 82 while the augmenting elongated member 16 is inserted between the first and second elongated members 12 and 14. The illustrated tethering system includes a pair of anchor wires or cables or filaments 84, each of which attaches to the proximal end region 52, 54 of one of the first and second elongated members 12 and 14. As best shown in FIGS. 5-7, each anchor wire 84 may include an enlarged end 88 (e.g., a generally spherical or ball-shaped end piece) that is at least partially received within a cavity 90 defined within the proximal end 52, 54 of the associated elongated member (FIG. 5). The thinner proximal or body portion of the anchor wire 84 extends through a retaining hole 92 (FIGS. 6 and 7) communicating with the cavity 90 while the enlarged end 88 is positioned within the cavity 90. The diameter of each retaining hole 92 is smaller than that of the associated enlarged end 88 to resist removal of the enlarged end 88 from the cavity 90 in a proximal direction.

The anchor wires 84 may provide little resistance to the deployment of the first and second elongated members 12 and 14, permitting the first and second elongated members 12 and 14 to exit the distal end 80 of the deployment cannula 82. The length and tension of the anchor wires 84 are adjustable to provide increased tension after the first and second elongated members 12 and 14 have exited the cannula 82. The anchor wires 84 keep the first and second elongated members 12 and 14 in close proximity to the distal end 80 of the cannula 82, thereby allowing the insertion of the augmenting elongated member 16 between the first and second elongated members 12 and 14 without having to increase the tension on the pull wire 74. This may be advantageous, as applying excessive tension to the pull wire 74 may move the first and second elongated members 12 and 14 to an undesirable curved configuration during insertion of the augmenting elongated member 16 therebetween.

After the implant 10 has been deployed and properly positioned, the anchor wires 84 may be detached from the first and second elongated members 12 and 14. In one embodiment, after the pull wire 84 has been removed from the implant 10 (e.g., by cutting it and applying a proximally directed force to both of its ends), a distally directed force may be applied to the implant 10 (e.g., pushing the implant 10 approximately 2 mm further from its deployed position) while the tension in the anchor wires 84 is maintained. Doing so effectively increases the tension on the anchor wires 84, which increased tension will cause the enlarged ends 88 of the anchor wires 84 to enter (FIG. 6) and pull through (FIG. 7) the smaller retaining holes 92 in the elongated members, thereby detaching the anchor wires 84 from the implant 10. Alternatively, a looped anchor wire (or wires) may be formed, such that a loop passes through holes or slots or openings in both of the first and second elongated members 12 and 14. The loop may then be cut by the user or break automatically like a mechanical fuse at the completion of insertion by the user cutting or otherwise severing the loop. In another embodiment, the loop may be configured to pull through or to cut through portions of the first and second elongated members 12 and 14 to detach without the loop being cut or severed.

As shown in FIG. 13, when the augmenting member 16 is positioned within the cannula 82, the pull wire 74 and anchor wires 84 may extend proximally beyond the augmenting elongated member 16 by occupying the space between the corners of the augmenting elongated member 16 and the corners of the cannula 82.

As noted above, the augmenting elongated member 16 may include a locking feature or mechanism or member in the form of a locking wire or cable or tether or filament 18, which is illustrated in FIGS. 12-18. The locking member 18 extends between a fixed end 94 (FIGS. 14, 17, and 18) and a free end 96. The fixed end 94 (which may be an enlarged ball or sphere) is secured at or adjacent to the proximal end 98 of the augmenting elongated member 16, positioned within an interior cavity or pocket 100 defined in the augmenting elongated member 16 at or adjacent to its proximal end 98. The interior cavity 100 may also receive a spacer or backstop 102, which will be described in greater detail herein.

An interior passage or lumen or cavity 104 communicates with the interior cavity 100, with the locking member 18 extending distally from the fixed end 94 through the interior passage 104. The interior passage 104 leads to the distal end 56 of the augmenting elongated member 16, where the locking member 18 exits the augmenting elongated member 16 and loops back toward the proximal end 98 of the augmenting elongated member 16, as shown in FIG. 12. The lateral side of the augmenting elongated member 16 includes a lateral groove 106 (best seen in FIG. 18) through which the locking member 18 extends as it loops back toward the proximal end 98 of the augmenting elongated member 16. The lateral groove 106 is located on the side of the augmenting elongated member 16 that will face radially inwardly when the distraction device 10 is fully deployed, such that the lateral groove 106 and the portion of the locking member 18 positioned therein communicate with the open interior or resident volume 108 defined by the generally annular distraction device 10.

Figure 17:
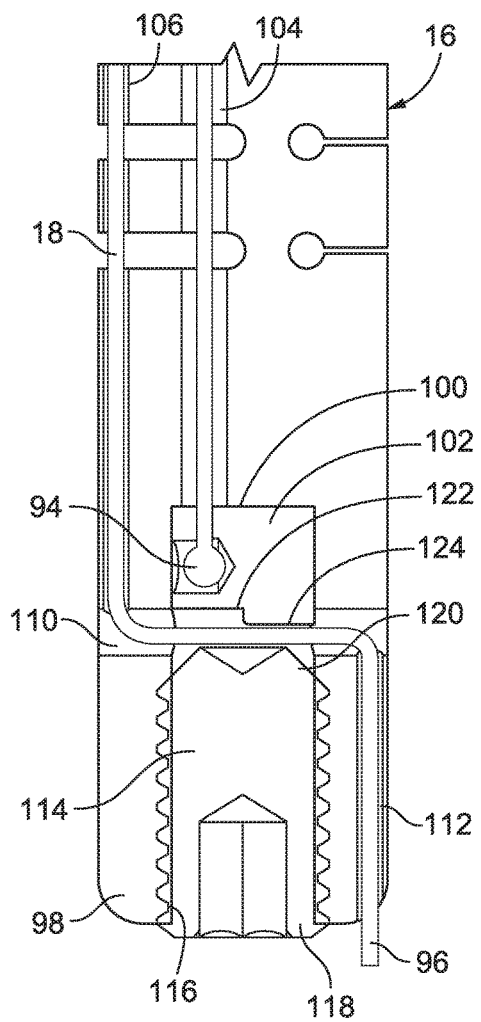
FIG. 17 is a cross-sectional top plan view of a proximal end of the augmenting elongated member of the distraction device of FIG. 1, with a locking member thereof in an initial condition.

At or adjacent to the proximal end 98 of the augmenting elongated member 16, the locking member 18 reenters the interior of the augmenting elongated member 16 from the lateral groove 106 via a bore 110 extending from one lateral side of the augmenting elongated member 16 toward the other lateral side, as shown in FIG. 17. As shown in FIG. 17, the bore 110 may extend all the way between the two lateral sides of the augmenting elongated member 16, but it is also within the scope of the present disclosure for the bore 110 to extend only partially through the width of the augmenting elongated member 16.

Figure 15:
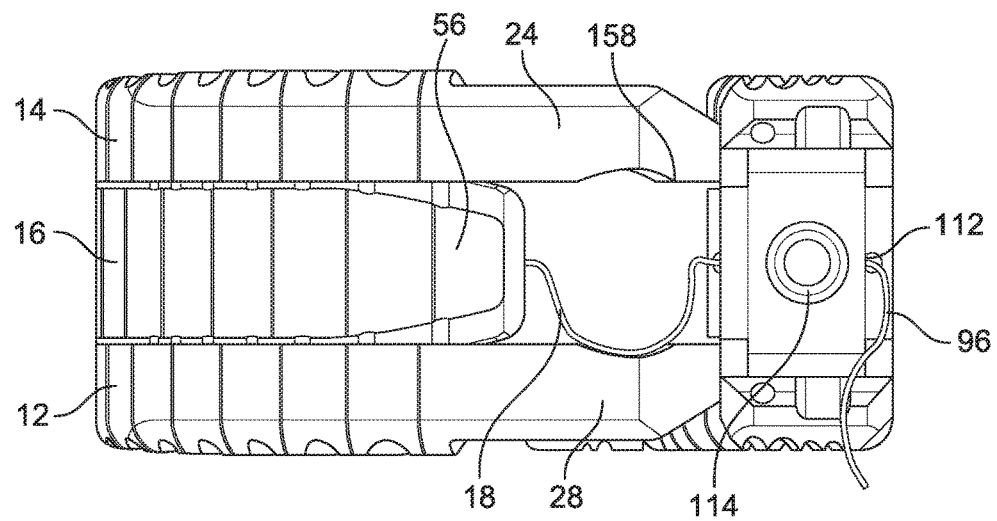
FIG. 15 is an end view of the distraction device of FIG. 1, with a locking member thereof in an unlocked condition.
Figure 16:
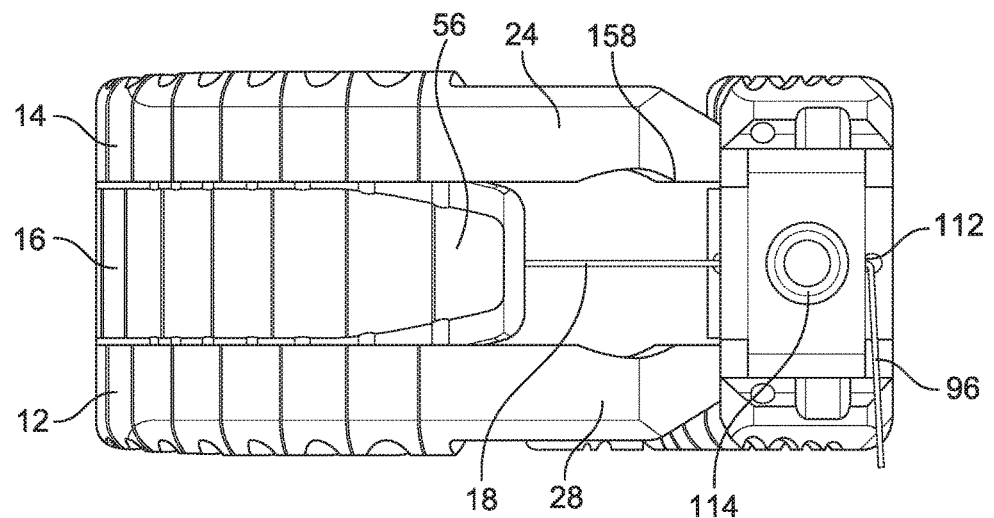
FIG. 16 is an end view of the distraction device of FIG. 1, with a locking member thereof in a locked condition.
Figure 18:
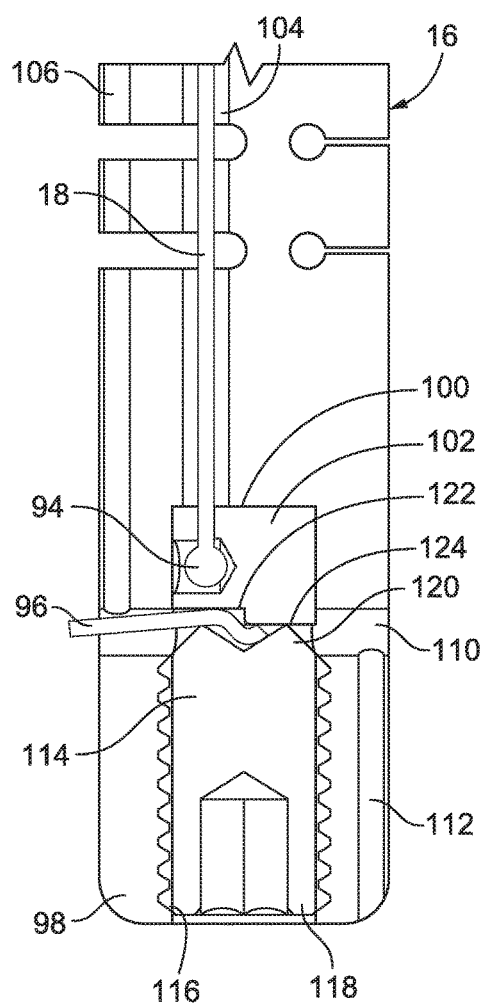
FIG. 18 is a cross-sectional top plan view of a proximal end of the augmenting elongated member of the distraction device of FIG. 1, with a locking member thereof in a locked condition.

In the illustrated embodiment, the bore 110 causes the locking member 18 to reenter the interior cavity 100 of the augmenting elongated member 16 in a region directly adjacent to the spacer 102, but separated from the fixed end 94 of the locking member 18 by the spacer 102. This portion of the locking member 18 extends along the width of the spacer 102 until it reaches a longitudinally extending bore 112 that communicates with the laterally extending bore 110, as best shown in FIG. 18. The free end 96 of the locking member 18 extends through the longitudinally extending bore 112 and exits the proximal end 98 of the augmenting elongated member 16 (FIG. 17), where it is accessible to apply tension to the locking member 18. For example, FIG. 15 shows the locking member 18 in an un-tensioned or moderately tensioned condition, while FIG. 16 shows the locking member 18 in a tensioned condition, with a pulling force applied to the portion of the free end 96 of the locking member 18 extending proximally out of the longitudinally extending bore 112. Applying tension to the free end 96 of the locking member 18 also causes the locking member 18 to separate from the lateral groove 106 and move through the open interior or resident volume 108 of the distraction device 10, as can be understood by comparing FIG. 17 to FIGS. 14 and 18.

The proximal end 98 of the illustrated augmenting elongated member 16 also includes a fastener 114 (e.g., a set screw) positioned within a longitudinal fastener bore 116 in communication with the spacer 102, with a portion of the free end 96 of the locking member 18 positioned between the fastener 114 and the spacer 102. The fastener 114 extends between an outer end 118 and an inner end 120 (FIGS. 17 and 18). The outer end 118 is configured to allow advancement of the fastener 114 in a distal direction into the fastener bore 116 toward the spacer 102. In a preferred embodiment, the outer perimeter of the fastener 114 and the surface of the fastener bore 116 include matching threads, in which case the outer end 118 of the fastener 114 is configured to accept a torque delivery tool or driver that rotates the fastener 114 to advance it distally into the fastener bore 116. In other embodiments, the fastener 114 may be advanced into the fastener bore 116 by non-rotational movement.

The inner end 120 of the fastener 114 is configured to have a cutting or shearing surface that severs the locking member 18 when brought into contact therewith with sufficient force. In the illustrated embodiment, the spacer 102 includes a retaining surface 122 and a cutting surface 124 facing the fastener 114 and separated by a step, with the cutting surface 124 positioned adjacent to and proximal of the retaining surface 122 (i.e., closer to the fastener 114), as shown in FIGS. 17 and 18. When the fastener 114 is sufficiently advanced into the fastener bore 116 (preferably, when it has been fully advanced into the fastener bore 116, which may be one full rotation when the fastener 114 is a threaded set screw), the inner end 120 of the fastener 114 comes into contact with the cutting surface 124 of the spacer 102, thereby severing the extra slack of the locking member 18 therebetween (FIG. 18) while maintaining the tension of the locking member 18. In contrast, the inner end 120 of the fastener 114 remains spaced away from the retaining surface 122 of the spacer 102, but sufficiently close so as to press the locking member 18 against the retaining surface 122, thereby effectively securing the locking member 18 to the spacer 102 of the augmenting elongated member 16 at that location.

By so securing the locking member 18 to the augmenting elongated member 16 at two locations (both of which are at or adjacent to the proximal end 98 of the augmenting elongated member 16 in the illustrated embodiment), the locking member 18 prevents the configuration of the augmenting elongated member 16 from changing. Locking the augmenting elongated member 16 into a particular configuration also effectively locks the first and second elongated members 12 and 14 (as well as the distraction device 10) into their current configuration, due to the locking relationship between the various elongated members, as described above. Preferably, the distraction device 10 is shaped into its final configuration prior to the fastener 114 locking the locking member 18 in place, thereby locking the distraction device 10 in its final configuration for long-term residence within the work space, as will be described in greater detail herein.

While the locking member 18 is described and illustrated as being associated with and secured to the augmenting elongated member 16, it should be understood that the locking member 18 may be associated with one of the other elongated members 12 and 14 and secured to multiple locations of either to lock the distraction device 10 in a particular configuration. Furthermore, it is also within the scope of the present disclosure for a plurality of similarly or differently configured locking members to be provided and associated with one or more of the elongated members. Additionally, rather than the locking member 18 being secured at multiple locations to an individual elongated member, it is also within the scope of the present disclosure for the locking member 18 to be secured at one location of one of the elongated members and at a second location of one of the other elongated members. For example, the locking member 18 may be secured to the augmenting elongated member 16 at a fixed end 94 and extend from the proximal end 98 of the augmenting elongated member 16 to exit the distal end 56 of the augmenting elongated member 16, as described above. After exiting the distal end 56 of the augmenting elongated member 16, the free end 96 of the locking member 18 may be secured to one of the other elongated members by any suitable means, rather than being secured at a second location of the augmenting elongated member 16. It should be understood that so securing the locking member 18 at separate locations of different elongated members will have a similar effect to securing the locking member 18 to separate locations of the same elongated member, in that the resulting distraction device 10 will be locked into a particular configuration.

The wires or cables or filaments or tethers described herein may consist of materials suitable for sterilization and compatible for temporary contact with animal, including human tissue. Metal wires may be made from stainless steel, Nitinol, or other suitable metal wires, for example. Non-metal wires may be made from natural fibers and polymeric fibers including polyethylene, UHPE, Victrex, PET, or similar medical-grade polymers.

Tensile forces may be applied to the wires or cables or filaments or lines described herein by any suitable source. In a preferred embodiment, the tensile forces are applied via a delivery device 126 (FIGS. 19 and 20), of which the deployment cannula 82 is the distal end. To the extent not contradicted by the present disclosure, delivery devices according to the present disclosure may be manufactured and configured generally according to the disclosure of U.S. Patent Application Publication No. 2008/0234687 to Schaller et al., which is incorporated herein by reference.

In the illustrated embodiment, the free ends of the various lines pass through the deployment cannula 82 to be attached to various attachment points located within the delivery device 126. The lines may be attached to the delivery device 126 by any of a number of suitable means, including releasable mechanical features such as screws, clamps, crimps, and ferrules and other like means. The lines may also be attached by knotting, gluing or pinching them to the delivery device 126.

In the illustrated embodiment, the pull wire 74 is associated with a slider 128 that is received within a central opening or cavity 130 of the delivery device 126 that is substantially coaxial with the deployment cannula 82. The slider 128 is movable along the longitudinal axis of the delivery device 126 within the central cavity 130 to adjust the tension in the pull wire 74, thereby adjusting the curvature of the first and second elongated members 12 and 14, as described above. In the illustrated embodiment, the outer surface of the slider 128 is threaded to engage threads of the central cavity 130, such that rotation of the slider 128 about its central axis will advance it proximally and distally through the central cavity 130. It is also within the scope of the present disclosure for the slider 128 to move with respect to the remainder of the delivery device 126 without rotating (e.g., by translational movement). If the slider 128 is configured to rotate while moving through the central cavity 130, an insertion knob 132 may be associated with the slider 128 and extend outside of the central cavity 130 to be rotated in order to rotate and move the slider 128 through the central cavity 130.

In the illustrated embodiment, the anchor wires 84 are associated with a capstan or spool or spindle 134, with the capstan 134 controlling the tension on the anchor wires 84. The capstan 134 may also limit the total amount of line released to hold the deployed first and second elongated members 12 and 14 at the desired location in close proximity to the distal end 80 of the cannula 82. The tension in the anchor wires 84 may also be controlled by other means such as springs, resilient means, sliding mechanisms, rotating mechanisms, moving mechanisms, pulleys, stretchable lines and the like.

The free end 96 of the locking member 18 may also be adjustably secured to a rotary mechanism (similar to the pull wire 74 and the anchor wires 84) or to a non-rotational component of the delivery device 126 or may extend through the delivery device 126 without being secured thereto.

As described above, after the distraction device 10 has been deployed, the pull wire 74 may be severed and removed. In the illustrated embodiment, the delivery device 126 includes a shearing assembly 136 (FIG. 21) for severing or cutting the pull wire 74 (or any of the other wires, as desired). The shearing assembly 136 includes a stationary member 138 that is fixedly secured to the delivery device 126 and a movable member 140 that is rotatably secured to the stationary member 138 (e.g., by a cap 142). The pull wire 74 (or any other wire to be severed by the shearing assembly 136) extends through the stationary and movable members 138 and 140. When it is desirable to sever the pull wire 74 (or any of the other wires or filaments described herein, such as the anchor wires 84), the movable member 140 is rotated with respect to the stationary member 138 to cut or shear or otherwise sever the pull wire 74. Another portion of the pull wire 74 may be secured at another location of the delivery device 126, such that proximal movement of the delivery device 126 (e.g., removing the delivery device 126 from the work space) will cause the pull wire 74 to withdraw from the first and second elongated member 12 and 14.

Figure 22:
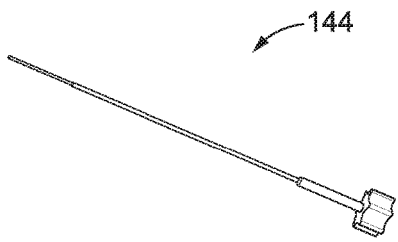
FIG. 22 is a perspective view of a pusher device suitable for use with the delivery device of FIG. 19.

A tool kit may include a number of related components and tools (illustrated in FIGS. 22-27) that may be used in connection with the delivery device 126. For example, FIG. 22 shows a pusher device or plunger 144 that may be used to push the augmenting elongated member 16 out of the deployment cannula 82 and into place between the first and second elongated members 12 and 14. The insertion knob 132 and slider 128 (if provided) may have central openings through which the pusher device 144 may extend to contact the proximal end 98 of the augmenting elongated member 16. In one embodiment, the distal end of the pusher device 144 is configured to engage and rotate the fastener 114 of the augmenting elongated member 16, as described above. In other embodiments, a separate device may be employed to advance the fastener 114 to the point that it severs and secures the free end 96 of the locking member 18.

Figure 23:
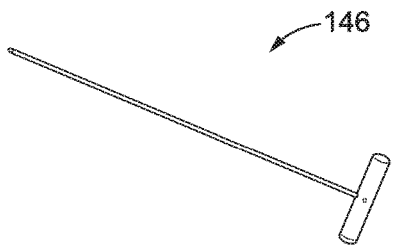
FIG. 23 is a perspective view of an extraction device suitable for use with the delivery device of FIG. 19.

FIG. 23 shows an extraction device 146 that may be used independently or in combination with the delivery device 126 to remove the distraction device 10 or an individual elongated member from the work space, if necessary.

Figure 24:
FIGS. 24 and 25 are perspective views of disc space sizing devices for determining the proper distraction device to deploy to a vertebral disc space.
Figure 25:

FIGS. 24 and 25 show disc space sizing devices or paddles 148 and 150 that may be used prior to introduction of the delivery device 126 to the disc space. According to conventional usage, the disc space sizing devices 148 and 150 are inserted into the disc space to determine the minimum and proper heights of the disc space. When the minimum and proper heights have been determined, the appropriate delivery device may be selected from a kit that includes a plurality of delivery devices of varying heights.

Figure 26:
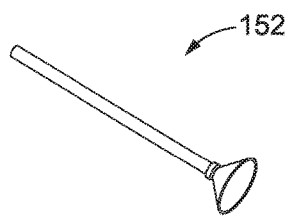
FIG. 26 is a perspective view of a funnel for use in delivering a bone filler material to the open interior of the distraction device of FIG. 1.
Figure 27:
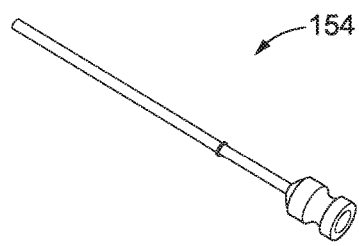
FIG. 27 is a perspective view of a tamp for use in combination with the funnel of FIG. 26.

FIGS. 26 and 27 show a funnel 152 and tamp 154 that may be used after the delivery device 126 has been removed from a work space to deliver a bone filler material 156 (FIG. 2) into the open interior or resident volume 108 of the distraction device 10, as will be described in greater detail herein. As used herein, "resident volume" refers generally to a structural characteristic of the support structure. The resident volume is a volume that is generally defined by the distraction device. The resident volume is preferably, but not necessarily, a volume completely enclosed by the distraction device, but can also be any volume generally defined by the distraction device. This term does not necessarily mean that the resident volume is an open or void volume or cavity and does not preclude a situation in which the resident volume is, at some point in time, filled with another material, such as bone graft, cement, therapeutic drugs or the like. It also does not preclude the resident volume from containing undisturbed human tissue that is located or remains within the resident volume during or after deployment of the distraction device. For example, if the distraction device is employed to separate adjoining soft tissue layers, such as subcutaneous fat and underlying muscle tissue, the resident volume of the distraction device support structure may be hollow or void of tissue after separation. On the other hand, if inserted into a spinal disc space, the resident volume may contain undisturbed disc tissue such as a portion of the nucleus pulposus or bone graft material placed before or after installation.

Figure 28:
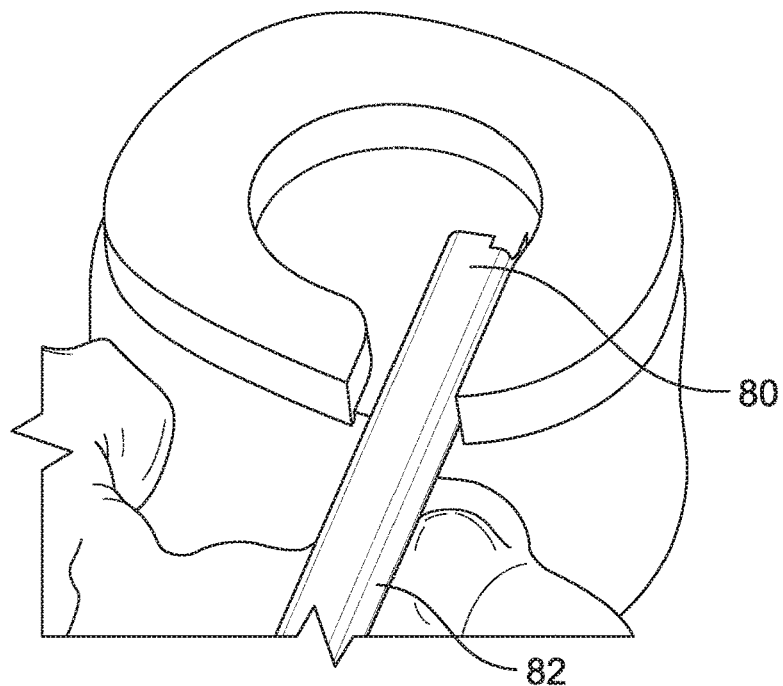
FIGS. 28-33 are perspective views illustrating a method of deploying the distraction device of FIG. 1 to a disc space.
Figure 29:
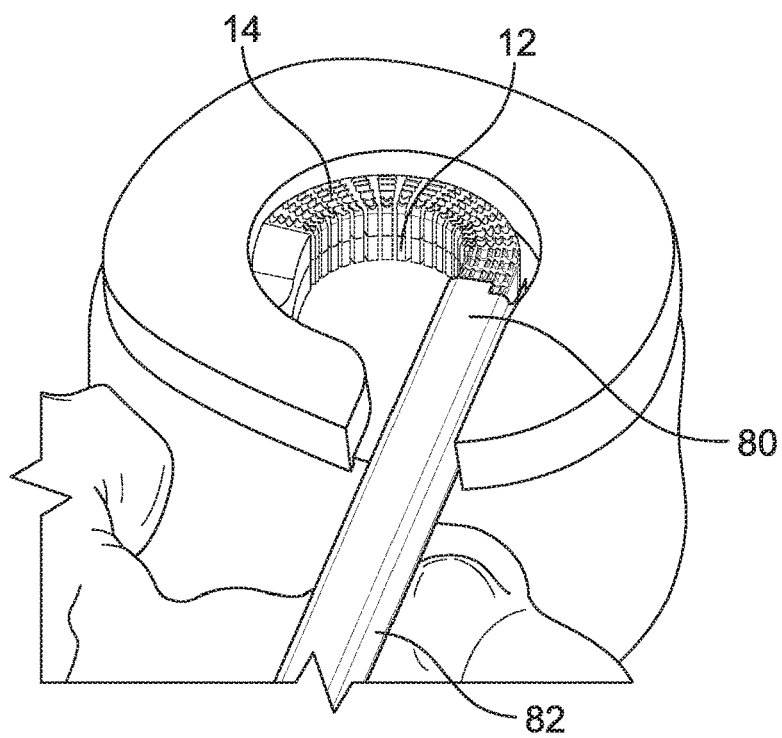

FIGS. 28-33 illustrate an exemplary method of inserting the distraction device 10 into a vertebral disc space, with FIG. 2 showing the fully installed distraction device 10. According to the illustrated method, an access port is made through the annulus of a vertebral disc using instruments and endoscopic or minimally invasive procedures generally known to those skilled in the art. The access port may be relatively small (e.g., no larger than the size of the deployment cannula 82), such that the procedure may be minimally invasive, with the resulting tissue distraction height being greater than the height of the access port. The location of the access port may vary without departing from the scope of the present disclosure, but it is preferred for the location of the access port be chosen so as to decrease the risk of nerve damage. In one embodiment (which is illustrated in FIG. 28), the access port is positioned so as to facilitate a transforaminal lumbar interbody fusion ("TLIF") approach, but other approaches may also be practiced without departing from the scope of the present disclosure. For example, according to another approach, the access port may be positioned so as to facilitate deployment of the elongated members through Kambin's triangle, which is defined by the exiting nerve root (the hypotenuse of the triangle), the superior border of the inferior vertebra (the base of the triangle), and the traversing nerve root (the height of the triangle). While this approach results in an access port that is positioned at a different location than in the illustrated TLIF approach, it should be understood that the method of inserting the elongated members so as to define the implant in situ (described below in greater detail) may be substantially the same.

Optionally, all or a portion of the nucleus pulposus is removed and the endplates of the adjacent vertebrae are scraped to cause bleeding and promote the fusion of bone graft material to the vertebral endplates. Sizing paddles 148, 150 (FIGS. 24 and 25) or like apparatus, may be slipped through the access port to determine the minimum disc height and the desired final disc height. Based on the minimum and desired final disc height measurement from the sizing paddles 148, 150, the physician chooses the deployment cannula and distraction device sizes. The maximum outer dimension of the deployment cannula 82 used to deliver the distraction device 10 is preferably similar or slightly smaller in height than the minimum disc height measured. Accounting for the cannula wall thickness and any gap between the cannula 82 and the top-to-bottom height of the first and second elongated members 12 and 14, the first and second elongated members 12 and 14 together are selected so as to be slightly less in height, top to bottom, than the minimum disc height.

When the appropriate deployment cannula 82 and distraction device 10 have been selected, a distal end 80 of the deployment cannula 82 is advanced through the access port and into the disc space (FIG. 28). The deployment cannula 82 may be part of a delivery device 126 of the type illustrated in FIGS. 19 and 20 and described above or any other suitable delivery device. The first and second elongated members 12 and 14 are pre-loaded at a distal region of the deployment cannula 82 in a generally linear configuration for simultaneous insertion into the disc space. The augmenting elongated member 16 may be similarly pre-loaded in the deployment cannula 82 in a generally linear configuration, but positioned proximally of the first and second elongated members 12 and 14 for insertion after the first and second elongated members 12 and 14.

Because the first and second elongated members 12 and 14 together clear the minimum disc height, they can be pushed out of the deployment cannula 82 and into the disc space easily using the delivery device 126 or the like. For delivery, the physician begins to push in the first and second elongated members 12 and 14 simultaneously out of the cannula 82 little by little, for example by using a pusher or plunger or other suitable actuating means, such as a rotary actuator. Between pushes, the physician may check the curvature of the partially inserted first and second elongated members 12 and 14 (FIG. 29) using X-ray or other visualization techniques to observe the position of the elongated members via radiopaque portions thereof (such as radiopaque markers embedded within the elongated members). By tensioning the pull wire 74, as described above, the physician adjusts the curvature of the first and second elongated members 12 and 14 in real time to closely follow the inner wall of the disc annulus.

Figure 30:
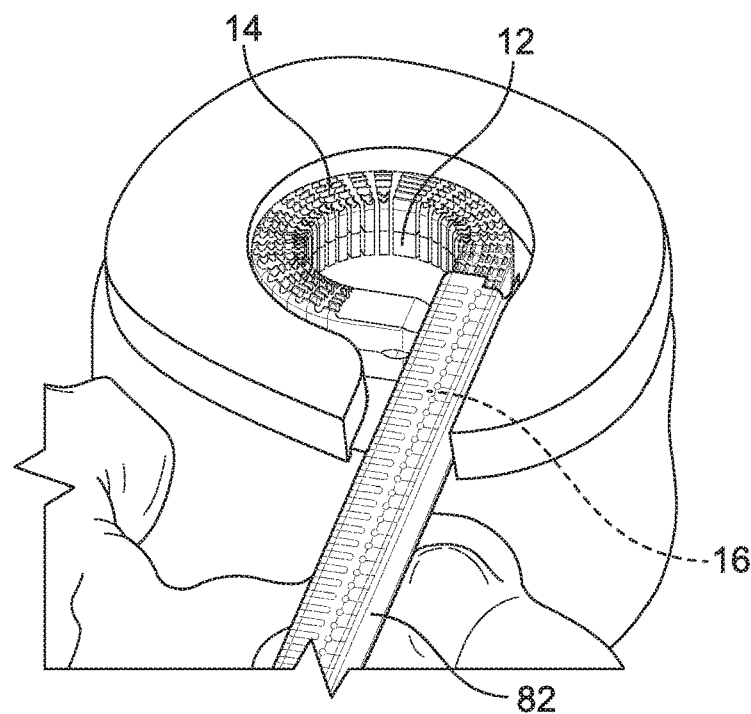

By the time the first and second elongated members 12 and 14 are entirely out of the cannula 82 and within the disc space, the distal or leading ends 28 and 24 of the first and second elongated members 12 and 14 may be adjacent to and/or in contact with the proximal ends 52 and 54 of the first and second elongated members 12 and 14. If not, additional tension may be applied to the pull wire 74 until the distal or leading end 28 and 24 of the first and second elongated members 12 and 14 are adjacent to and/or in contact with the proximal ends 52 and 54 of the first and second elongated member 12 and 14. As shown in FIG. 30, the fully inserted first and second elongated members 12 and 14 define a generally less linear or generally annular configuration prior to the augmenting elongated member 16 being inserted therebetween.

With the first and second elongated members 12 and 14 fully deployed from the cannula 82 and in the generally annular configuration of FIG. 30, they are held to the leading or distal end 80 of the cannula 82 by the tension in the pull wire 74 and/or the anchor wires 84. The physician then advances the augmenting elongated member 16 out of the cannula 82 (or, if the augmenting elongated member 16 is not pre-loaded in the cannula 82, the physician loads the augmenting elongated member 16 into the delivery system and then advances it out of the cannula 82). The augmenting elongated member 16 is received between the first and second elongated members 12 and 14 and follows the path or generally less linear shape defined by the first and second elongated members 12 and 14 until it has been at least partially (but most preferably fully) inserted therebetween. The locking features described above, if provided, may assist the augmenting elongated member 16 in following the path defined by the first and second elongated member 12 and 14, while also preventing the first and second elongated members 12 and 14 from disengaging with the augmenting elongated member 16. While inserting the augmenting elongated member 16, the physician should be careful to maintain the cannula 82 in place, as the location of the cannula 82 effects the placement of the first and second elongated members 12 and 14 and, hence, the resulting distraction device 10. The physician may check the alignment of all of the elongated members during insertion of the augmenting elongated member 16 using X-ray or other visualization techniques.

When first advanced out of the cannula 82, the augmenting elongated member 16 begins to wedge itself in between the first and second elongated members 12 and 14. Depending on the thickness (height) of the augmenting elongated member 16, some slack may need to be given at this point to the pull wire 74 and/or the anchor wires 84 to allow them to separate in a vertical direction (i.e., in a direction between the surfaces to be distracted or along the axis of the spine or the direction of distraction) to allow further advancement of the augmenting elongated member 16.

Once the physician confirms that the tip of the augmenting elongated member 16 is wedged securely and the raised ribs 48 and 50 and associated grooves 42 and 46 (if provided) of the three elongated members are engaged, the augmenting elongated member 16 is advanced slowly while checking for changes in the curvature of the distraction device 10. As before, the curvature can be adjusted in real time using the pull wire 74. In a preferred embodiment, the curvature may be adjusted automatically by developing tension in the pull wire 74 via a screw or rotational mechanism incorporated into or associated with the slider 128. The augmenting elongated member 16 is preferably pushed in all the way until its back face is flush with the back faces of the first and second elongated members 12 and 14 (FIG. 31), at which point the augmenting elongated member 16 may be fully locked in place with respect to the first and second elongated members 12 and 16.

The physician then makes a final check of the implant placement and desired distraction. If satisfied, the physician detaches the pull wire 74 and anchor wires 84 from the implant 10 (as described above) and may remove the cannula 82 and associated delivery device 126. Even with the pull wire 74 detached from the implant 10, the reaction force applied to the implant 10 by the tissues being distracted should be sufficient to maintain the implant 10 in the illustrated generally annular configuration.

Figure 31:
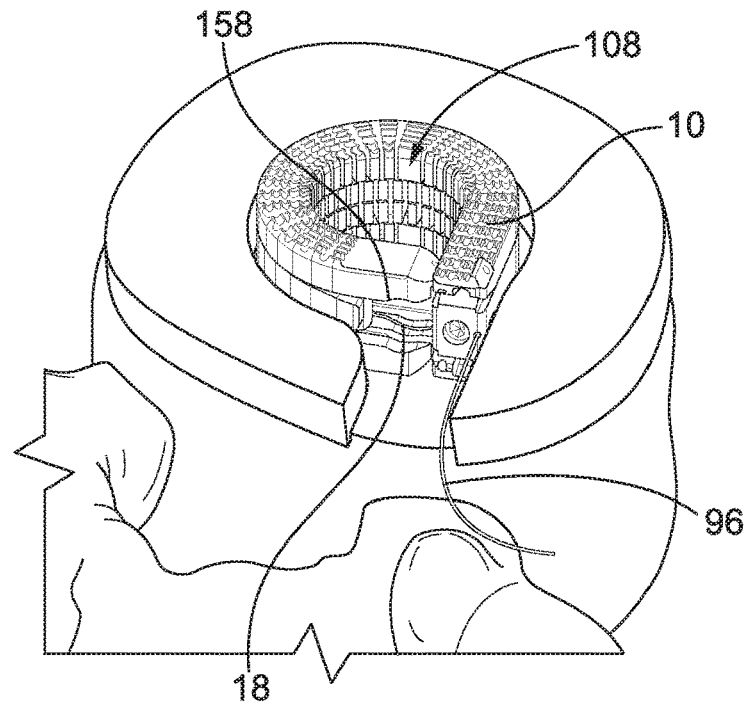

As shown in FIG. 31, the augmenting elongated member 16 may have a linear extent that is less than the linear extents of the first and second elongated members 12 and 14 in the insertion or longitudinal direction (i.e., in a dimension extending between the proximal and distal ends of the elongated members). Thus, when the augmenting elongated member 16 has been fully inserted between the first and second elongated members 12 and 14 (such that their back faces are substantially flush), the augmenting elongated member 16 will define a generally less linear configuration that extends over a lesser arc than the generally complete circle defined by the first and second elongated members 12 and 14. In particular, the augmenting elongated member 16 defines a generally arcuate, non-annular configuration when fully inserted, such that a window 158 is defined between the proximal and distal ends 98 and 56 of the augmenting elongated member 16 (which define lateral sides of the window 158) and the distal ends 28 and 24 of the first and second elongated members 12 and 14 (which define lower and upper sides of the window 158, respectively).

The locking member 18, as described above, may separate from the lateral groove 106 in which it sits during (or after) insertion of the augmenting elongated member 16 to extend through the open interior or resident volume 108 defined by the implant 10. At this point, it may be advantageous for the locking member 18 to not be fully tensioned, otherwise it may obstruct the window 158, as shown in FIG. 16. As described above, the reaction forces applied to the fully expanded implant 10 by the opposing tissue surfaces should be sufficient to maintain the shape of the implant 10 even without shaping force being applied by the pull wire 74 or the locking member 18. However, it may be preferred for some amount of tension to be applied to the locking member 18 to remove it from the resident volume 108 and position it in the window 158, but with sufficient slackness that the locking member 18 does not extend across the middle of the window 158. Instead, it may be preferred for the locking member 18 to hang slack within the window 158, as shown in FIGS. 15 and 31, to allow a funnel 152 (FIG. 32) to extend through the window 158 and access the resident volume 108 without contacting the locking member 18.

Figure 32:
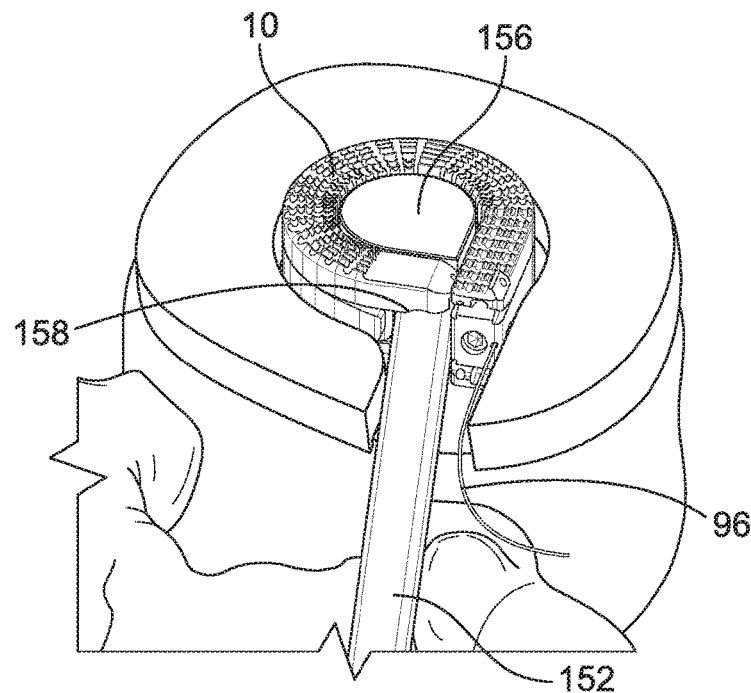

As shown in FIG. 32, if bone graft material or bone filler material 156 is needed, it can be injected or otherwise introduced into the open interior or resident volume 108 defined by the implant 10 via the window 158 defined in the side wall of the implant 10. In the illustrated embodiment, the distal end of a funnel 152 is inserted through the window 158 and then bone graft material or bone filler material 156 is advanced through the funnel 152 and into the resident volume 108 using a tamp 154 of the type shown in FIG. 27 or the like. FIG. 32 shows the resident volume 108 being substantially entirely filled with bone graft material or bone filler material 156, but it is also within the scope of the present disclosure for the resident volume 108 to be only partially filled with bone graft material or bone filler material 108. An advantage of implants according to the present disclosure is that, unlike most other expandable cages, bone graft material or bone filler material it meant to be place through the window defined in the side wall of the implant and make full contact on the two tissue surfaces to be distracted. Some expandable cage-type implants include bone graft material within the cage as it is introduced into the disc space, and then expand the cage, which tends to leave voids between the bone graft material and the tissue surfaces to be distracted. Voids in bone graft are undesirable, as they may inhibit fusion or the rate of fusion between vertebral endplates.

Figure 33:
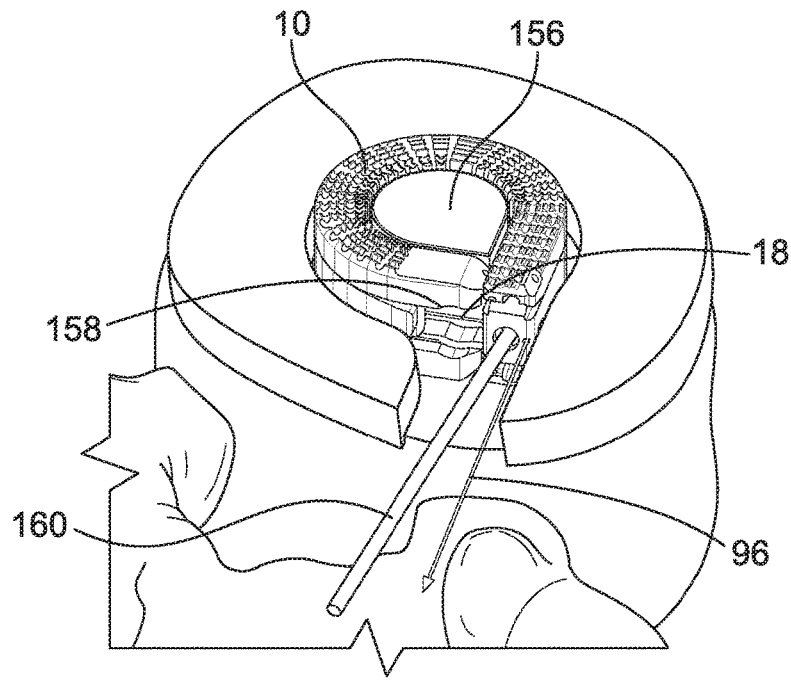

When the desired amount of bone graft material or bone filler material 156 has been introduced into the resident volume 108, the physician withdraws the funnel 152 and then applies a proximally directed force to the free end 96 of the locking member 18 (FIG. 33). Tension is applied to the locking member 18 until it is taut or tightly drawn across the middle of the window 158 (FIG. 16). Then, the fastener 114 of the augmenting elongated member 16 is advanced so as to sever the free end 96 of the locking member 18, while securing the locking member 18 to the augmenting elongated member 16 at a second location, as described in greater detail above. The fastener 114 may be advanced by a driver device 160 (FIG. 33) that pushes or rotates or otherwise actuates the fastener 114 so as to move it distally with respect to the augmenting elongated member 16 into contact with the locking member 18.

The free end 96 of the locking member 18 being secured and severed, the severed portion may be removed from the disc space, along with the driver device 160, leaving only the fully deployed implant 10 in the disc space, as shown in FIG. 2. Thereafter, the access port may be closed, along with any other access points opened to reach the disc space.

Figure 34:
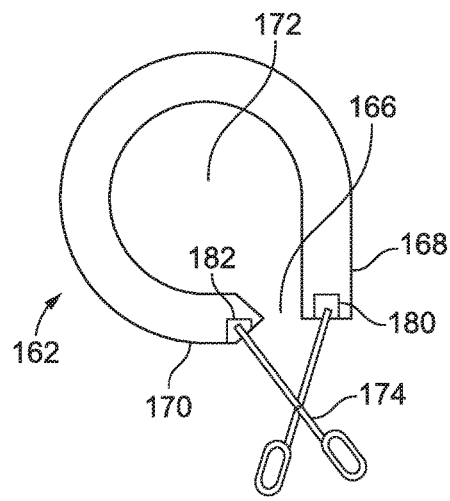
FIG. 34 is a top plan view of an alternative embodiment of an elongated member or distraction device according to the present disclosure.
Figure 35:
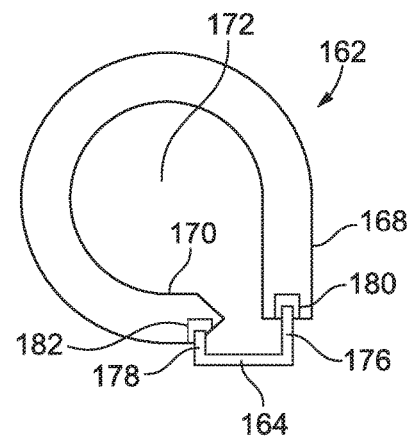
FIG. 35 is a top plan view of the elongated member or distraction device of FIG. 34, with a fixture or fastener securing the proximal and distal ends of the elongated member or distraction device.

It should be understood that the above-described elongated members, distraction device, deployment tools, and methods are merely exemplary. For example, FIGS. 34 and 35 illustrate an alternative embodiment of an elongated member or distraction device 162 employing a different locking mechanism or member 164 (FIG. 35). In the illustrated embodiment, the elongated member or distraction device 162 is moved from a generally linear configuration to a generally less linear configuration (e.g., as described above using a pull wire or the like) with the elongated member or distraction device 162 assuming an arcuate, but not closed loop or annular, shape. The gap 166 between the proximal and distal ends 168 and 170 of the elongated member or distraction device 162 may be used to introduce bone graft material or the like into the resident volume 172 defined by the elongated member or distraction device 162. When the surgeon desires to close the gap 166, the proximal and distal ends 168 and 170 are drawn together (e.g., using a closure tool 174 that engages the proximal and distal ends 168 and 170 to bring them toward each other) and a fastener or fixture 164 is secured to the ends 168 and 170 to prevent them from separating. In one embodiment, the fastener or fixture 164 comprises a staple with two prongs 176 and 178 that are received within cavities 180 and 182 of the proximal and distal ends 168 and 170 to close the gap 166 and maintain the elongated member or distraction device 162 in a generally annular configuration.

Figure 36:
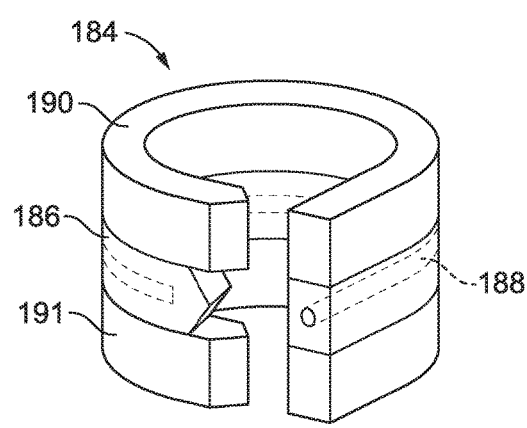
FIG. 36 is a perspective view of a distraction device having an elongated member with shape memory properties.

In other embodiments, a separate fastener or fixture is not required to maintain the elongated member or distraction device in a generally annular configuration. For example, FIG. 36 shows a distraction device 184 in which one of the constituent elongated members (shown as the augmenting elongated member 186) includes an embedded wire or tube or elongated element 188 made of a material having shape memory properties, such as Nitinol or a shape memory polymer. The embedded element 188 preferably has a natural or pre-set shape, for example, the illustrated arcuate or annular configuration. When the augmenting elongated member 186 is present in a deployment cannula, it is constrained to a generally linear configuration, allowing for an easy and minimally invasive deployment of the elongated members into the work space. Because of the shape memory properties of the embedded element 188, the augmenting elongated member 186 will return to its natural curved or annular shape once the constraint is removed (i.e., once the distal end of the augmenting elongated member 186 exits the distal end portion of the cannula and enters the work space). Rather than being embedded within the augmenting elongated member 186, the shape memory material may instead be secured to an outer surface (e.g., a lateral side) of the augmenting elongated member 186. In other embodiments, one or both of the upper and lower elongated members 190 and 191 includes shape memory properties in addition to (or instead of) the augmenting elongated member 186 having shape memory properties. By providing one or more of the elongated members with shape memory properties, the need to use a locking member or fastener or fixture to secure the resulting distraction device in its generally less linear, deployed configuration is avoided.

Figure 37:
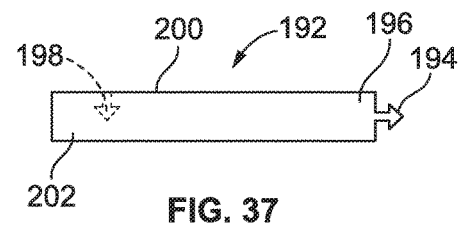
FIG. 37 is a top plan view of an elongated member or distraction device configured to maintain a generally annular configuration without a separate locking member or fastener or fixture.
Figure 38:
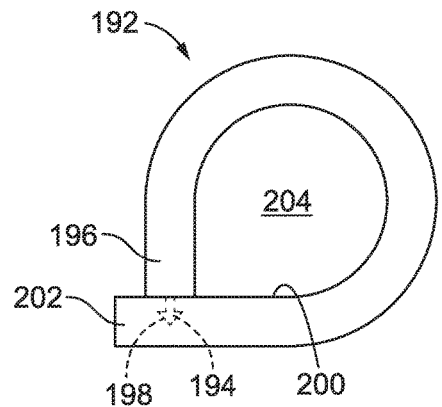
FIG. 38 is a top plan view of the elongated member or distraction device of FIG. 37, in a generally annular configuration.

FIGS. 37 and 38 illustrate another embodiment of an elongated member or distraction device 192 that may maintain a generally less linear, deployed configuration without the need for a separate fixture or fastener or locking member. The illustrated elongated member or distraction device 192 includes an integrally formed locking projection or extension 194 at its distal end 196 and a similarly shaped cavity or pocket 198 along a lateral side 200 at or adjacent to its proximal end 202. The cavity 198 is preferably associated with the lateral side 200 of the elongated member or distraction device 192 toward which the elongated member or distraction device 192 curves when deployed in a work space. In the illustrated embodiment, the elongated member or distraction device 192 may be moved from a generally linear configuration to a generally less linear configuration (e.g., as described above using a pull wire or the like) with the elongated member or distraction device 192 assuming an arcuate, but not closed loop or annular, shape with a gap between the proximal and distal ends 202 and 196. The gap between the proximal and distal ends 202 and 196 of the elongated member or distraction device 192 may be used to introduce bone graft material or the like into the resident volume 204 defined by the elongated member or distraction device 192. When the surgeon desires to close the gap, the locking projection 194 is pressed into and retained by the cavity 198, as shown in FIG. 38. In the illustrated embodiment, the locking projection 194 is generally conical, which may promote retention of the projection 194 within the cavity 198, but other locking projection configurations (e.g., an enlarged spherical shape) may also be employed without departing from the scope of the present disclosure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A tissue distraction device comprising:
   first and second elongated members, each elongated member defining a closed loop in a separate plane in a deployed configuration; and
   an augmenting elongated member fully received between the first and second elongated members in the deployed configuration and having a length that is less than the length of each of the first and second elongated members.

2. The tissue distraction device of claim 1, wherein the augmenting, first, and second elongated members cooperate to define a window into an interior of the tissue distraction device.

3. The tissue distraction device of claim 2, wherein the window is configured to allow for the introduction of a bone filler material into the interior of the tissue distraction device through the window.

4. The tissue distraction device of claim 2, further comprising a locking member secured to the augmenting elongated member at a plurality of locations to lock the augmenting elongated member in a generally arcuate configuration, wherein a portion of the locking member extends across the window.

5. The tissue distraction device of claim 4, further comprising a fastener, wherein
   the locking member extends between a fixed end and a free end,
   the fixed end of the locking member is secured at or adjacent to a proximal end of the augmenting elongated member, and
   the fastener secures the free end of the locking member to the augmenting elongated member at or adjacent to the proximal end of the augmenting elongated member.

6. The tissue distraction device of claim 1, wherein the first, second, and augmenting elongated members combine to define a structure having a non-uniform thickness configured to adjust the lordotic angle of the spine.

7. The tissue distraction device of claim 1, wherein
   each of the first and second elongated members extends between proximal and distal ends and includes a lateral side, and
   one of the ends of the first elongated member contacts the lateral side of the first elongated member adjacent to the other end of the first elongated member, and
   one of the ends of the second elongated member contacts the lateral side of the second elongated member adjacent to the other end of the second elongated member.

8. The tissue distraction device of claim 1, wherein each elongated member is generally rectangular in cross-sectional shape and defined by elongated upper and lower surfaces, proximal and distal ends, and elongated lateral side surfaces.

9. The tissue distraction device of claim 8, wherein each of the elongated members includes
   a longitudinally extending wall,
   a plurality of similarly shaped first teeth extending laterally from the wall in one direction, and
   a plurality of similarly shaped second teeth extending laterally from the wall in an opposite direction and differently configured from said first teeth.

10. A tissue distraction device comprising:
    first and second elongated members insertable between tissue layers and adapted to define a structure in situ having a dimensional aspect dimension in a direction extending between the tissue layers; and
    an augmenting elongated member insertable between and in contact with said first and second elongated members to spread the first and second elongated members apart to increase the dimension of at least a portion of the structure in situ, wherein
    each elongated member is generally rectangular in cross-sectional shape and defined by elongated upper and lower surfaces, proximal and distal ends, and elongated lateral side surfaces,
    each elongated member is sufficiently flexible to change between a generally linear first configuration and a second configuration that is less linear than the first configuration, and
    the augmenting elongated member has a length that is less than the length of each of the first and second elongated members.

11. The tissue distraction device of claim 10, wherein each of the elongated members includes
    a longitudinally extending wall,
    a plurality of similarly shaped first teeth extending laterally from the wall in one direction, and
    a plurality of similarly shaped second teeth extending laterally from the wall in an opposite direction and differently configured from said first teeth.

12. The tissue distraction device of claim 10, wherein
    the proximal end of each of the first and second elongated members is ramped, and
    the distal end of the augmenting elongated member is tapered to engage and separate the first and second elongated members when the augmenting elongated member is inserted therebetween.

13. The tissue distraction device of claim 10, wherein the augmenting elongated member is configured to cooperate with said first and second elongated members to define a window into an interior of the tissue distraction device when the augmenting elongated member is inserted between and in contact with said first and second elongated members and the elongated members are in the second configuration.

14. The tissue distraction device of claim 13, further comprising a locking member configured to be secured to the augmenting elongated member at a plurality of locations to lock the augmenting elongated member in the second configuration in which a portion of the locking member extends across the window.

15. The tissue distraction device of claim 14, further comprising a fastener, wherein
    the locking member extends between a fixed end and a free end,
    the fixed end of the locking member is secured at or adjacent to a proximal end of the augmenting elongated member, and
    the fastener is configured to secure the free end of the locking member to the augmenting elongated member at or adjacent to the proximal end of the augmenting elongated member when the augmenting elongated member is in the second configuration.

16. The tissue distraction device of claim 10, wherein the first, second, and augmenting elongated members are configured to combine to define a structure having a non-uniform thickness configured to adjust the lordotic angle of the spine.

17. The tissue distraction device of claim 10, wherein one of the ends of the first elongated member is configured to contact one of the lateral sides of the first elongated member adjacent to the other end of the first elongated member when the first elongated member is in the second configuration, and one of the ends of the second elongated member is configured to contact one of the lateral sides of the second elongated member adjacent to the other end of the second elongated member when the second elongated member is in the second configuration.

18. The tissue distraction device of claim 10, wherein each of the first and second elongated members is configured to define a closed loop in the second configuration.

19. The tissue distraction device of claim 18, wherein the augmenting elongated member is configured to define a generally arcuate configuration in the second configuration.

20. The tissue distraction device of claim 10, wherein each of the first and second elongated members is configured to define a closed loop in the second configuration, the augmenting elongated member is configured to cooperate with said first and second elongated members to define a window into an interior of the tissue distraction device in the second configuration, and the window is configured to allow for the introduction of a bone filler material into the interior of the tissue distraction device in the second configuration through the window.

* * * * *